(12) United States Patent
Pozzi et al.

(10) Patent No.: US 9,937,174 B2
(45) Date of Patent: Apr. 10, 2018

(54) COMBINATIONS OF HISTONE DEACETYLASE INHIBITORS AND BENDAMUSTINE

(71) Applicant: University of Modena and Reggio Emilia, Modena (IT)

(72) Inventors: Samantha Pozzi, Modena (IT); Maria Cosenza, Modena (IT)

(73) Assignee: UNIVERSITY OF MODENA AND REGGIO EMILIA, Modena (IT)

(*) Notice: Subject to any disclaimer, the term of this patent is extended or adjusted under 35 U.S.C. 154(b) by 0 days.

(21) Appl. No.: 14/959,473

(22) Filed: Dec. 4, 2015

(65) Prior Publication Data

US 2016/0158232 A1    Jun. 9, 2016

Related U.S. Application Data

(60) Provisional application No. 62/087,868, filed on Dec. 5, 2014.

(51) Int. Cl.
*A61K 31/505* (2006.01)
*A61K 31/4184* (2006.01)
*A61K 45/06* (2006.01)

(52) U.S. Cl.
CPC ........ *A61K 31/505* (2013.01); *A61K 31/4184* (2013.01); *A61K 45/06* (2013.01)

(58) Field of Classification Search
CPC ... A61K 31/4184; A61K 31/505; A61K 45/06
USPC ....................................................... 514/275
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 | 4/2012 | van Duzer et al. | |
| 8,394,810 B2 | 3/2013 | van Duzer et al. | |
| 8,609,678 B2 | 12/2013 | van Duzer et al. | |
| 8,614,223 B2 | 12/2013 | van Duzer et al. | |
| 8,785,470 B2* | 7/2014 | Castro ................. | C07D 401/14 514/266.1 |
| 9,096,549 B2 | 8/2015 | van Duzer et al. | |
| 9,139,583 B2 | 9/2015 | van Duzer et al. | |
| 9,145,412 B2 | 9/2015 | van Duzer et al. | |
| 9,492,423 B2* | 11/2016 | Loury ................. | A61K 31/343 |
| 2004/0266769 A1 | 12/2004 | Bressi et al. | |
| 2005/0119305 A1 | 6/2005 | Naka et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0152254 A1 | 6/2010 | Bialer et al. | |
| 2010/0168463 A1 | 7/2010 | Hirata et al. | |
| 2010/0330197 A1 | 12/2010 | Higashiguchi et al. | |
| 2011/0218154 A1 | 9/2011 | Schreiber et al. | |
| 2012/0121502 A1 | 5/2012 | Van Duzer et al. | |
| 2013/0225543 A1 | 8/2013 | Jones et al. | |
| 2014/0011767 A1 | 1/2014 | Yang et al. | |
| 2014/0120083 A1* | 5/2014 | Stern ...................... | A61K 31/00 424/133.1 |
| 2014/0142104 A1 | 5/2014 | van Duzer et al. | |
| 2014/0142117 A1 | 5/2014 | van Duzer et al. | |
| 2014/0357512 A1 | 12/2014 | Jones et al. | |
| 2015/0045380 A1 | 2/2015 | van Duzer et al. | |
| 2015/0099744 A1 | 4/2015 | Yang et al. | |
| 2015/0105358 A1 | 4/2015 | Quayle et al. | |
| 2015/0105383 A1 | 4/2015 | Quayle et al. | |
| 2015/0105384 A1 | 4/2015 | Jones et al. | |
| 2015/0105409 A1 | 4/2015 | Quayle et al. | |
| 2015/0150871 A1 | 6/2015 | Quayle et al. | |
| 2015/0176076 A1 | 6/2015 | Yang et al. | |
| 2015/0239869 A1 | 8/2015 | Mazitschek et al. | |
| 2015/0299130 A1 | 10/2015 | van Duzer et al. | |

FOREIGN PATENT DOCUMENTS

| | | |
|---|---|---|
| EP | 2 524 918 A1 | 11/2012 |
| WO | 2001/070675 A2 | 9/2001 |
| WO | 2002/074298 A1 | 9/2002 |
| WO | 2003/037869 A1 | 5/2003 |
| WO | 2003/076401 A1 | 9/2003 |

(Continued)

OTHER PUBLICATIONS

Butler et al. (2000) "Suberoylanilide Hydroxamic Acid, an Inhibitor of Histone Deactetylase, Suppresses the Growth of Prostate Cancer Cells in Vitro and in Vivo," Cancer Research. 60:5165-5170.
Costello et al. (Dec. 2012) "Evidence for Changes in RREB-1, ZIP3, and Zinc in the Early Development of Pancreatic Adenocarcinoma," J. Gastrointest. Canc. 43:570-578.
Dokmanovic et al. (2007) "Histone Deacetylase Inhibitors: Overview and Perspectives," Mol. Cancer Res. 5( 10):981-989.
Giannini et al. (Jul. 2012) "Histone Deacetylase Inhibitors in the Treatment of Cancer: Overview and Perspectives," Future Med. Chem. 4(11):1439-1460.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.

(Continued)

*Primary Examiner* — My-Chau T. Tran
(74) *Attorney, Agent, or Firm* — Lathrop Gage LLP; Brian C. Trinque

(57) ABSTRACT

The invention relates to pharmaceutical combinations comprising an HDAC inhibitor and bendamustine; pharmaceutical compositions comprising the same; and methods of using such combinations and compositions for treating lymphoma in a subject in need thereof.

12 Claims, 26 Drawing Sheets

(56) References Cited

FOREIGN PATENT DOCUMENTS

| WO | 2003/076430 A1 | 9/2003 |
|---|---|---|
| WO | 2004/052869 A1 | 6/2004 |
| WO | 2005/012261 A1 | 2/2005 |
| WO | 2005/028447 A1 | 3/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/055068 A2 | 5/2008 |
| WO | 2008/091349 A1 | 7/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/080996 A1 | 7/2010 |
| WO | 2010/131922 A2 | 11/2010 |
| WO | 2011/011186 A1 | 1/2011 |
| WO | 2011/019393 A2 | 2/2011 |
| WO | 2011/084991 A2 | 7/2011 |
| WO | 2011/091213 A2 | 7/2011 |
| WO | 2011/146855 A1 | 11/2011 |
| WO | 2013/013113 A2 | 1/2013 |
| WO | 2013/039488 A1 | 3/2013 |
| WO | 2013/040286 A2 | 3/2013 |

OTHER PUBLICATIONS

Lane et al. (2009) "Histone Deacetylase Inhibitors in Cancer Therapy," J. Clin. Oncol. 27:5459-5468.
Loudni et al. (2007) "Design, synthesis and biological evaluation of 1, 4-benzodiazepine-2, 5-dione-based HDAC inhibitors," Bioorganic and Medicinal Chemistry Letters. 17:4819-4823.
Mazitschek et al. (2008) "Development of a Fluorescence Polarization Based Assay for Histone Deacetylase Ligand Discovery," Bioorganic and Medicinal Chemistry Letters. 18(9):2809-2812.
Miller et al. (1998) "Paclitaxel as the Initial Treatment of Multiple Myeloma: An Eastern Cooperative Oncology Group Study (E1A93)," Am. J. Clin. Oncol. 21(6):553-556.
Perez (1998) "Paclitaxel in Breast Cancer," The Oncologist. 3:373-389.
Ropero et al. (2007) "The Role of Histone Deacetylases (HDACs) in Human Cancer," Molecular Oncology. 1:19-25.
Smil et al. (2009) "Novel HDAC6 Isoform Selective Chiral Small Molecule Histone Deacetylase Inhibitors," Bioorganic and Medicinal Chemistry Letters. 19:688-692.
Sporn et al. (2000) "Chemoprevention of Cancer," Carcinogenesis. 21(3):525-530.
Thoppil et al. (Sep. 2011) "Terpenoids as Potential Chemopreventive and Therapeutic Agents in Liver Cancer," World J. Hepatol. 3(9)228-249.
International Search Report with Written Opinion corresponding to International Patent Application No. PCT/US2011/021982, dated Oct. 10, 2011.
Search Opinion corresponding to European Patent Application No. 11735212, dated Jun. 26, 2014.
Written Opinion corresponding to Singapore Patent Application No. Application No. 201205393-0, dated Nov. 15, 2013.
Acetylon Pharmaceuticals, Inc. (Dec. 1, 2014) "Acetylon's Selective HDAC Inhibitors to be Featured in Multiple Presentations of Positive Clinical and Preclinical Data at the 56th ASH Annual Meeting and Exposition," Press Release. MacDougall Biomedical Communications. Accessible on the Internet at URL: http://www.acetylon.com/docs/Acetylon_ASH_2014_Alert_FINAL_120114.pdf.
Cosenza et al. (Dec. 17, 2014) "Preclinical Screening of the HDAC6 Inhibitor Roclininostat (ACY-1215) Combined with Bendamustine in Lymphoma Cell Lines," In; The 56th ASH Annual Meeting and Exposition. Abstract No. 3124.
International Search Report with Written Opinion corresponding to International Patent Application No. PCT/IB2015/002609, dated Apr. 20, 2016.
Angibaud et al. (2005) "Discovery of Pyrimidyl-5-hydroxamic acids as New Potent Histone Deacetylase Inhibitors," European Journal of Medicinal Chemistry. 40(6):597-606.
Brana et al. (2002) "Synthesis and biological evaluation of novel 2-(1H-imidazol-4-yl)cyclopropane carboxylic acids: key intermediated for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32(11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Neidle, Stephen: Ed. (2008) Cancer Drug Design and Discovery. Elsevier/Academic Press. pp. 427-431.
Pellicciari et al. (1996) "Synthesis and Pharmacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated May 21, 2013.
International Search Report with Written Opinion corresponding to International Patent Application No. PCT/US2011/060791, dated Jun. 12, 2012.
Supplementary European Search Report corresponding to European Application No. 11840803.8, dated Mar. 5, 2014.

\* cited by examiner

COMBINATIONS OF HISTONE DEACETYLASE INHIBITORS AND BENDAMUSTINE

CROSS-REFERENCE TO RELATED APPLICATIONS

This application claims priority to U.S. Provisional Application Ser. No. 62/087,868, filed Dec. 5, 2014, which is incorporated herein by reference in its entirety.

BACKGROUND

B-cell lymphoma and T-cell lymphoma remain incurable and progressive diseases that continue to rank as leading causes of mortality in patients with these diseases.

Histone deacetylases (HDACs) are promising targets for cancer therapy. They are a family of enzymes that deacetylate lysine residues on histone and non-histone proteins, which play a role in regulating cell cycle progression and survival. Unfortunately, non-selective HDAC inhibitors have led to dose-limiting toxicities in patients. Ricolinostat is a novel selective histone deacetylase 6 (HDAC6) inhibitor. HDAC6 is a class IIB histone deacetylase that plays an important role in the cellular response to environmental stress.

Bendamustine is an antineoplastic drug designed to combine the properties of a purine analogue and an alkylating agent.

Due to the dose-limiting toxicities of the above therapies, there is an ongoing need in the art for more efficacious and less toxic compositions and methods for the treatment of lymphoma. In order to meet these needs, provided herein are pharmaceutical combinations comprising an HDAC inhibitor and bendamustine, and methods for the treatment of lymphoma. The combinations and methods of the invention are well tolerated and do not exhibit the dose-limiting toxicities of prior therapies.

SUMMARY OF THE INVENTION

Provided herein are pharmaceutical combinations for the treatment of lymphoma in a subject in need thereof. Also provided herein are methods for treating lymphoma in a subject in need thereof.

Provided in some embodiments are combinations comprising a histone deacetylase (HDAC) inhibitor and bendamustine for the treatment of lymphoma in a subject in need thereof. For example, an embodiment of the invention provides a pharmaceutical combination for treating lymphoma comprising a therapeutically effective amount of a histone deacetylase 6 (HDAC6) specific inhibitor or a pharmaceutically acceptable salt thereof, and bendamustine or a pharmaceutically acceptable salt thereof. An additional embodiment of the invention provides a pharmaceutical combination for treating lymphoma comprising a therapeutically effective amount of a histone deacetylase 6 (HDAC6) specific inhibitor or a pharmaceutically acceptable salt thereof, and bendamustine or a pharmaceutically acceptable salt thereof, wherein the combination is administered at dosages exhibiting a synergistic effect.

Provided in other embodiments are methods for treating lymphoma in a subject in need thereof comprising administering to the subject an effective amount of a combination comprising a histone deacetylase (HDAC) inhibitor and bendamustine. For example, an embodiment of the invention provides a method for treating lymphoma in a subject in need thereof comprising administering to the subject a therapeutically effective amount of a pharmaceutical combination comprising a histone deacetylase 6 (HDAC6) specific inhibitor or a pharmaceutically acceptable salt thereof, and bendamustine or a pharmaceutically acceptable salt thereof. An additional embodiment of the invention provides a method for treating lymphoma in a subject in need thereof comprising administering to the subject a therapeutically effective amount of a pharmaceutical combination comprising a histone deacetylase 6 (HDAC6) specific inhibitor or a pharmaceutically acceptable salt thereof, and bendamustine or a pharmaceutically acceptable salt thereof, wherein the combination is administered at dosages exhibiting a synergistic effect.

In specific embodiments, the HDAC6-specific inhibitor is a compound of Formula I:

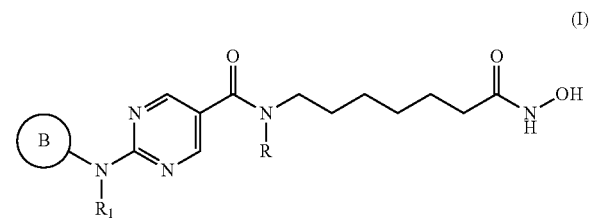

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl; and R is H or $C_{1-6}$-alkyl.

In preferred embodiments, the compound of Formula I is:

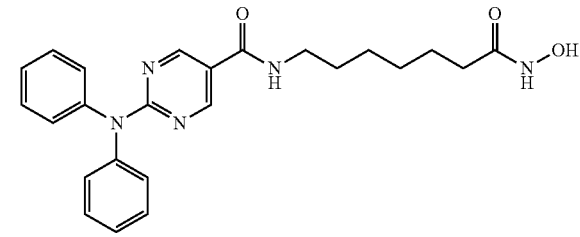 [SMILES: O=C(CCCCCCNC(=O)c1cnc(N(c2ccccc2)c2ccccc2)nc1)NO]

or a pharmaceutically acceptable salt thereof.

In yet other embodiments, the compound of Formula I is:

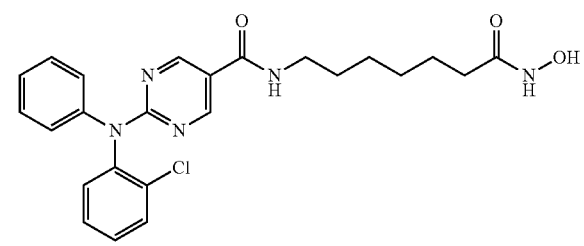 [SMILES: O=C(CCCCCCNC(=O)c1cnc(N(c2ccccc2)c2ccccc2Cl)nc1)NO]

or a pharmaceutically acceptable salt thereof.

In other specific embodiments, the HDAC6-specific inhibitor is a compound of Formula II:

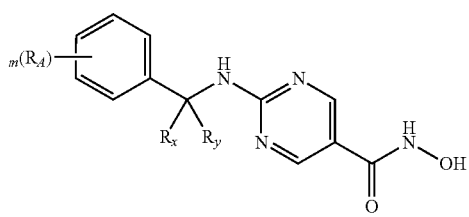

(II)

or a pharmaceutically acceptable salt thereof,
wherein, $R_x$ and $R_y$, together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2.

In preferred embodiments, the compound of Formula II is:

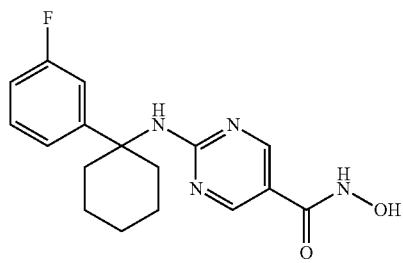 [SMILES: O=C(NO)c1cnc(NC2(c3cccc(F)c3)CCCCC2)nc1]

or a pharmaceutically acceptable salt thereof.

In other preferred embodiments, the compound of Formula II is:

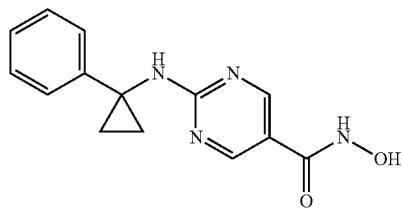 [SMILES: O=C(NO)c1cnc(NC2(c3ccccc3)CC2)nc1]

or a pharmaceutically acceptable salt thereof.

In some embodiments, the HDAC inhibitor and bendamustine are administered with a pharmaceutically acceptable carrier.

In some embodiments, the HDAC inhibitor and bendamustine are administered in separate dosage forms. In other embodiments, the HDAC inhibitor and bendamustine are administered in a single dosage form.

In some embodiments, the HDAC inhibitor and bendamustine are administered at different times. In other embodiments, the HDAC inhibitor and bendamustine are administered at substantially the same time.

In some embodiments, the combination of a HDAC inhibitor and bendamustine achieves a synergistic effect in the treatment of the subject in need thereof.

Another embodiment of the invention includes a method for inducing apoptosis of a cancer cell comprising administering to the cell a combination comprising an HDAC inhibitor and bendamustine. In some embodiments, the induction of apoptosis is associated with an increase in reactive oxygen species. In some embodiments, the apoptosis is associated with the activation of caspase 3, caspase 9, caspase 8, and/or PARP.

Yet another embodiment of the invention includes a method for reducing the viability of a cancer cell comprising administering to the cell a combination comprising an HDAC inhibitor and bendamustine.

Still another embodiment of the invention includes a method for reducing clonogenic survival of a cancer cell comprising administering to the cell a combination comprising an HDAC inhibitor and bendamustine.

A further embodiment of the invention includes a method for suppressing cell proliferation in a cancer cell comprising administering to the cell a combination comprising an HDAC inhibitor and bendamustine.

Another embodiment of the invention includes a method for reducing the expression of Bcl-2 in a cancer cell comprising administering to the cell a combination comprising an HDAC inhibitor and bendamustine.

Another embodiment of the invention includes a method for increasing expression of the cell cycle proteins p21 and p27, and decreasing expression of the cell cycle protein cyclin D in a cancer cell comprising administering to the cell a combination comprising an HDAC inhibitor and bendamustine.

Another embodiment of the invention includes a method for inducing dephosphorylation of PI3K/Akt signalling pathways in a cancer cell comprising administering to the cell a combination comprising an HDAC inhibitor and bendamustine.

Other objects, features, and advantages will become apparent from the following detailed description. The detailed description and specific examples are given for illustration only because various changes and modifications within the spirit and scope of the invention will become apparent to those skilled in the art from this detailed description. Further, the examples demonstrate the principle of the invention.

BRIEF DESCRIPTION OF THE FIGURES

FIG. 5A shows representative dot plot of WSU-NHL cells upon treatment with ricolinostat (1, 2, 5, 10 µM) alone for 24 h and staining by annexin V/propidium iodide.

FIG. 5B shows percentages of apoptotic cells in WSU-NHL, Hut-78 and Jeko-1 cell lines after 24-48 h of exposure to ricolinostat alone (1, 2, 5 and 10 µM).

FIG. 5C shows representative dot plot of WSU-NHL and Hut-78 treated with ricolinostat (4 µM) in combination with bendamustine (20 µM) for 24 h and Jeko-1 cells treated with the combination of 5 µM ricolinostat and 50 µM bendamustine. The flow cytometry shows an increase of apoptosis induced by combination treatment.

FIG. 5D shows percentages of apoptotic cells (early and late apoptosis) treated with combination of 4 µM ricolinostat (R) and 20 µM bendamustine (B) for WSU-NHL and Hut-78 and with combination of 5 µM ricolinostat and 50 µM bendamustine for Jeko-1 cells.

FIG. 5E shows representative data (%) of ROS generation from WSU-NHL, Hut-78 and Jeko-1 treated with the ricolinostat (1, 5, 10 µM) alone for 24 hours. All data are expressed as the mean±SD of triplicate culture.

FIG. 6A shows representative data of ROS generation from WSU-NHL after treatment with ricolinostat (R) and bendamustine (B) for 24.

FIG. 6B shows the percentage of cells with increased ROS level from drug combination. The co-administration of the antioxidant NAC blocked the increase of ROS generation. $H_2O_2$ was used as a positive control.

FIG. 6C shows ROS generation induced by the drug combination were linked with a decrease of Thioredoxin-1 (Trx1) expression. Western blot of cellular extracts from WSU-NHL, Hut-78 and Jeko-1 cells probed with antibody against Trx-1.

FIG. 6D shows drug combination mediated ER stress and UPR signaling. Representative western blots of cellular extracts from WSU-NHL, Hut-78 and Jeko-1 treated with the drugs alone or in combination at the indicated doses for 24 h. Tubulin was used to normalize protein loading.

DETAILED DESCRIPTION

Figure 1A:
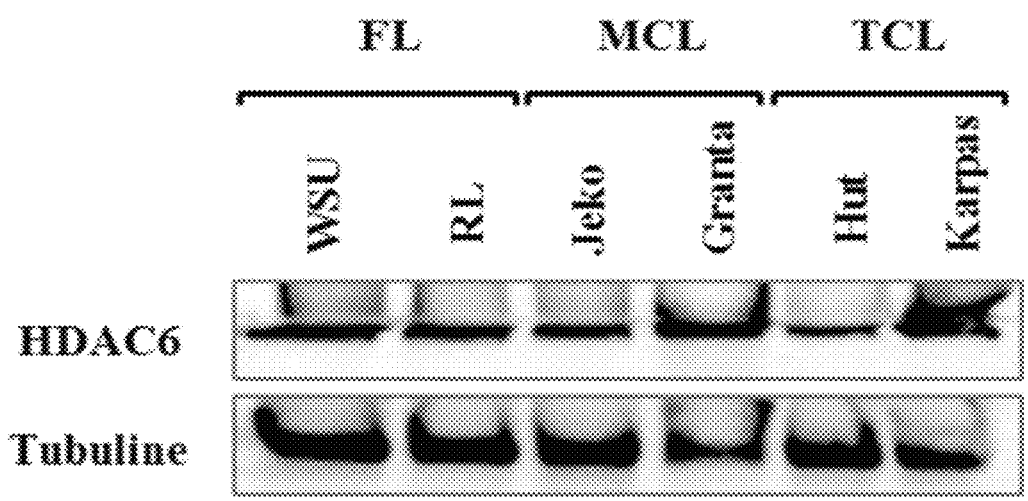
FIG. 1A shows that HDAC6 is highly expressed in all cell lines examined

The instant application is directed, generally, to combinations comprising a histone deacetylase (HDAC) inhibitor and bendamustine, and methods for the treatment of lymphoma.

Definitions

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "halo" refers to a halogen, such as fluorine, chlorine, bromine, and iodine.

The term "combination" refers to two or more therapeutic agents to treat a therapeutic condition or disorder described in the present disclosure. Such combination of therapeutic agents may be in the form of a single pill, capsule, or intravenous solution. However, the term "combination" also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6-specific" means that the compound binds to HDAC6 to a substantially greater extent, such as about 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6-specific. On the other hand, a compound that binds to HDAC6 with an $IC_{50}$ of 50 nM and to HDAC1 with an $IC_{50}$ of 60 nM is not HDAC6-specific.

The term "inhibitor" is synonymous with the term antagonist.

Histone Deacetylase (HDAC) Inhibitors

Provided herein are pharmaceutical combinations for the treatment of lymphoma in a subject in need thereof. Also provided herein are methods for treating lymphoma in a subject in need thereof.

The combinations and methods of the invention comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 inhibitor.

In some embodiments, the HDAC6-specific inhibitor is a compound of Formula I:

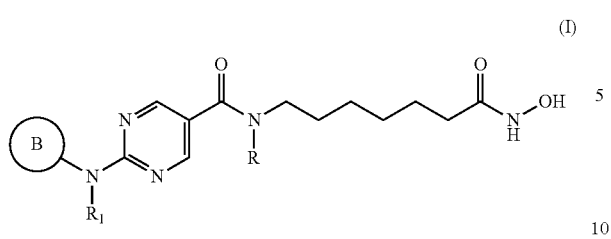

(I)

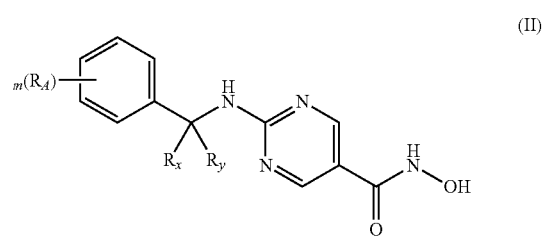

(II)

or a pharmaceutically acceptable salt thereof,
wherein, ring B is aryl or heteroaryl;

$R_1$ is an aryl or heteroaryl, each of which may be optionally substituted by OH, halo, or $C_{1-6}$-alkyl; and R is H or $C_{1-6}$-alkyl.

Representative compounds of Formula I include, but are not limited to:

or a pharmaceutically acceptable salt thereof,
wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2.

Representative compounds of Formula II include, but are not limited to:

Compound A

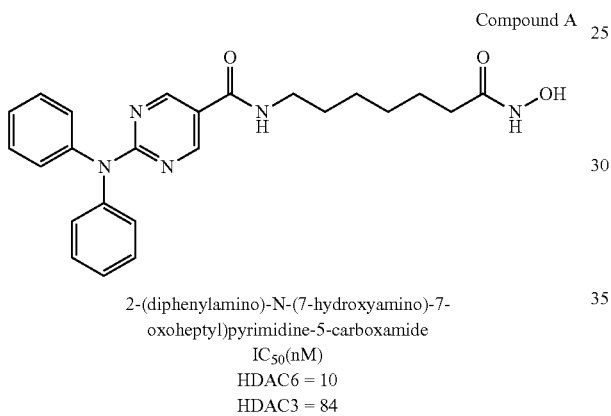

2-(diphenylamino)-N-(7-hydroxyamino)-7-oxoheptyl)pyrimidine-5-carboxamide
$IC_{50}$(nM)
HDAC6 = 10
HDAC3 = 84

Compound B

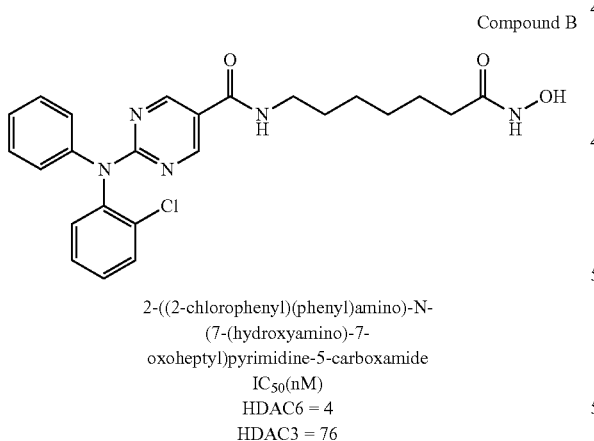

2-((2-chlorophenyl)(phenyl)amino)-N-(7-(hydroxyamino)-7-oxoheptyl)pyrimidine-5-carboxamide
$IC_{50}$(nM)
HDAC6 = 4
HDAC3 = 76 or pharmaceutically acceptable salts thereof.

The preparation and properties of selective HDAC6 inhibitors according to Formula I are provided in International Patent Application No. PCT/US2011/021982 (WO/2011/091213), the entire content of which is incorporated herein by reference.

In other embodiments, the HDAC6-specific inhibitor is a compound of Formula II:

Compound C

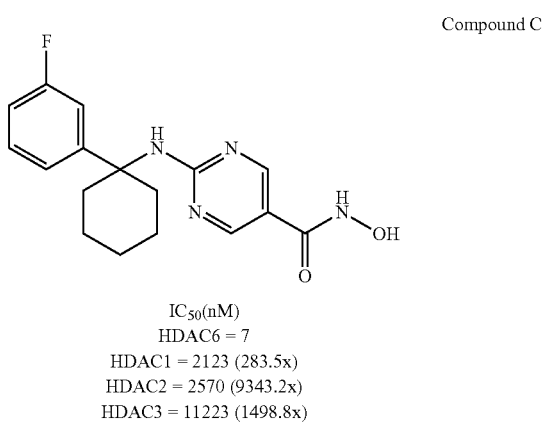

$IC_{50}$(nM)
HDAC6 = 7
HDAC1 = 2123 (283.5x)
HDAC2 = 2570 (9343.2x)
HDAC3 = 11223 (1498.8x)

Compound D

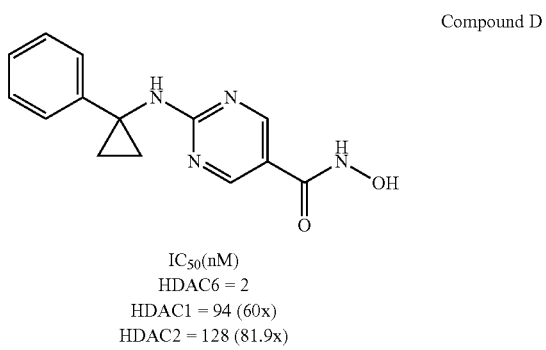

$IC_{50}$(nM)
HDAC6 = 2
HDAC1 = 94 (60x)
HDAC2 = 128 (81.9x)
HDAC3 = 219 (139.5x)

or pharmaceutically acceptable salts thereof.

The preparation and properties of selective HDAC6 inhibitors according to Formula II are provided in International Patent Application No. PCT/US2011/060791 (WO/2012/068109), the entire content of which is incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Bendamustine

The combinations and methods of the invention comprise bendamustine, or a pharmaceutically acceptable salt thereof:

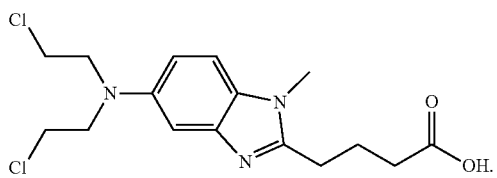 [SMILES: Cn1c(CCCC(=O)O)nc2cc(N(CCCl)CCCl)ccc21]

Bendamustine, 4-[5-[Bis(2-chloroethyl)amino]-1-methylbenzimidazol-2-yl]butanoic acid, is a nitrogen mustard synthesized in 1963. Its synthesis is described in German Patent Nos. 34727 and 159877, and more recently in International Publication No. WO2010/042568. Bendamustine has since been used to treat, e.g., chronic lymphocytic leukemia, Hodgkin's disease, non-Hodgkin's lymphoma, multiple myeloma, and breast cancer. Bendamustine is typically administered by injection. Pharmaceutical compositions comprising bendamustine are described in, e.g., U.S. Pat. Nos. 8,436,190, 8,609,863, 8,791,270, and 8,895,756. Solid forms of bendamustine are described in, e.g., U.S. Pat. Nos. 8,445,524, 8,669,279, and 8,883,836. The content of each of these patent documents is hereby incorporated by reference in its entirety.

In an embodiment of any of the combinations or methods provided herein, the bendamustine is bendamustine hydrochloride.

In some embodiments, the compounds described herein are unsolvated. In other embodiments, one or more of the compounds are in solvated form. As known in the art, the solvate can be any of pharmaceutically acceptable solvent, such as water, ethanol, and the like.

Although the compounds of bendamustine and Formulas I and II are depicted in their neutral forms, in some embodiments, these compounds are used in a pharmaceutically acceptable salt form. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Another embodiment is an isotopically labeled compound of any of the compounds delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

Combinations/Pharmaceutical Combinations

Provided herein are combinations for the treatment of lymphoma in a subject in need thereof. Provided in some embodiments are combinations comprising a histone deacetylase (HDAC) inhibitor and bendamustine, or a pharmaceutically acceptable salt thereof, for the treatment of lymphoma in a subject in need thereof. Combinations of an HDAC inhibitor, and bendamustine, or a pharmaceutically acceptable salt thereof, will also be referred to herein as a "combination of the invention."

In some embodiments of the combinations, the HDAC inhibitor is an HDAC6 inhibitor, or an HDAC6-specific inhibitor.

In certain embodiments, the HDAC6-specific inhibitor is a compound of Formula I:

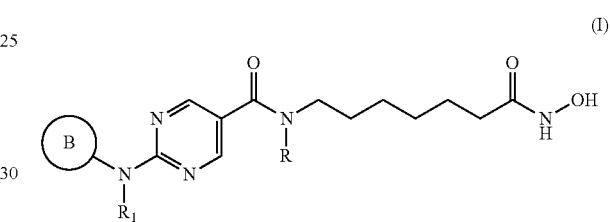

or a pharmaceutically acceptable salt thereof.

In preferred embodiments, the compound of Formula I is:

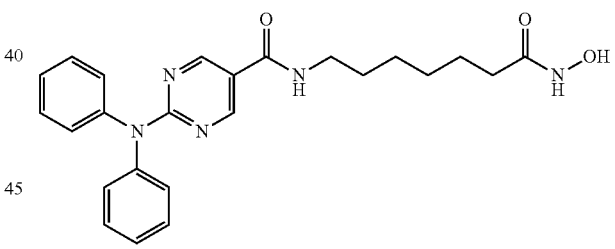

or a pharmaceutically acceptable salt thereof.

In yet other embodiments, the compound of Formula I is:

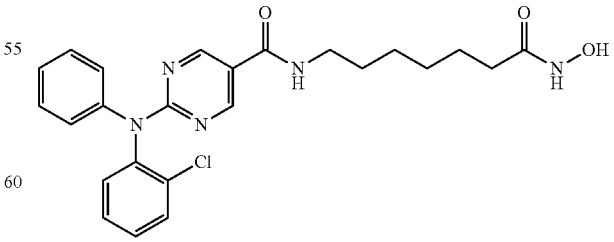

or a pharmaceutically acceptable salt thereof.

In other specific embodiments, the HDAC6-specific inhibitor is a compound of Formula II:

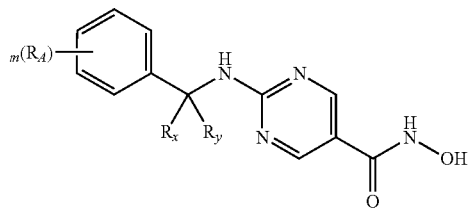

(II)

or a pharmaceutically acceptable salt thereof.

In preferred embodiments, the compound of Formula II is:

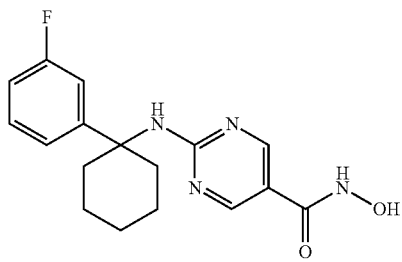 [SMILES: O=C(NO)c1cnc(NC2(c3cccc(F)c3)CCCCC2)nc1]

or a pharmaceutically acceptable salt thereof.

In other preferred embodiments, the compound of Formula II is:

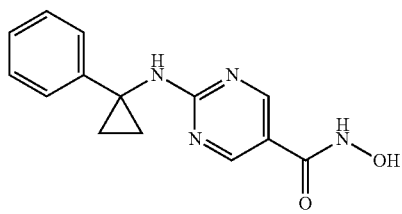 [SMILES: O=C(NO)c1cnc(NC2(c3ccccc3)CC2)nc1]

or a pharmaceutically acceptable salt thereof.

In one embodiment, provided herein is a combination therapy comprising an HDAC6-specific inhibitor and bendamustine or a pharmaceutically acceptable salt thereof, wherein the HDAC6-specific inhibitor is a compound of Formula I:

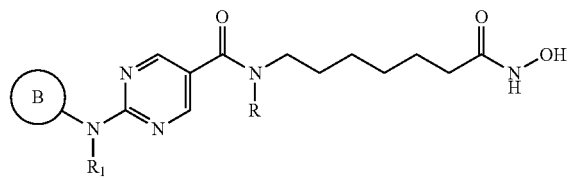

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

In specific embodiments of the combinations, the HDAC6-specific inhibitor is:

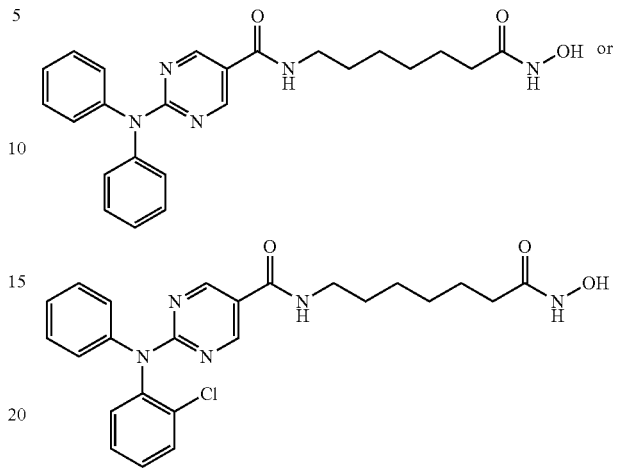

or pharmaceutically acceptable salts thereof.

In another embodiment, provided herein is a combination therapy comprising an HDAC6-specific inhibitor and bendamustine, or a pharmaceutically acceptable salt thereof, wherein the HDAC6-specific inhibitor is a compound of Formula II:

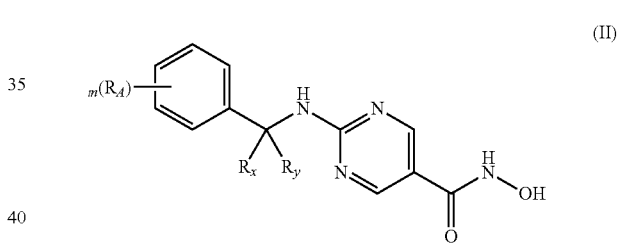

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.

In specific embodiments of the combinations, the HDAC6-specific inhibitor is:

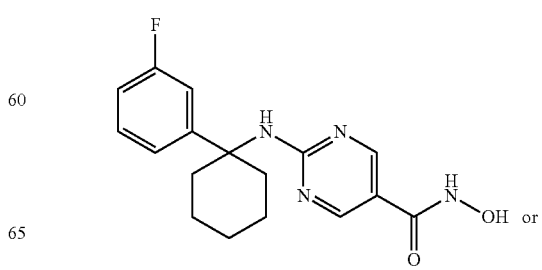

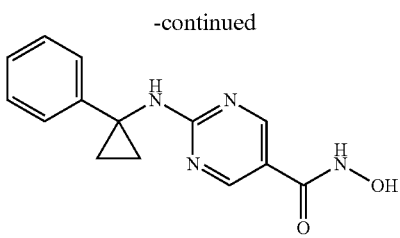

or a pharmaceutically acceptable salt thereof.

Pharmaceutical Compositions

In another aspect, provided herein is a pharmaceutical composition, such as a combined preparation, which comprises the combination of the invention, i.e., an HDAC inhibitor (e.g., compounds of formulae I or II, or pharmaceutically acceptable salts thereof) and bendamustine, or a pharmaceutically acceptable salt thereof. In an embodiment, the pharmaceutical composition further comprises one or more excipients. In an embodiment, the pharmaceutical composition further comprises one or more pharmaceutically acceptable excipients.

As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

In an embodiment of the pharmaceutical composition, the molar ratio of the HDAC inhibitor or a pharmaceutically acceptable salt thereof to bendamustine or a pharmaceutically salt thereof, is at about 1:100 to about 1:1. For example, the molar ratio can be about 1:100, about 1:95, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:15, about 1:10, about 1:8, about 1:6, about 1:5, about 1:4, about 1:3, about 1:2, or about 1:1. In certain embodiments, the molar ratio is about 1:50 to about 1:2. In other embodiments, the molar ratio is about 1:20 to about 1:2. In further embodiments, the molar ratio is about 1:10 to about 1:2. In yet other embodiments, the molar ratio is about 1:5.

Administration/Dose

In some embodiments of the combination therapy, the HDAC inhibitor (a compound of Formula I or II) is administered simultaneously with bendamustine. Simultaneous administration typically means that both compounds enter the patient at precisely the same time. However, simultaneous administration also includes the possibility that the HDAC inhibitor and bendamustine enter the patient at different times, but the difference in time is sufficiently miniscule that the first administered compound is not provided the time to take effect on the patient before entry of the second administered compound. Such delayed times typically correspond to less than 2 minutes, and more typically, less than 1 minute or less than 30 seconds. In one example, wherein the compounds are in solution, simultaneous administration can be achieved by administering a solution containing the combination of compounds. In another example, simultaneous administration of separate solutions, one of which contains the HDAC inhibitor and the other of which contains bendamustine, can be employed. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising bendamustine.

In other embodiments, the HDAC inhibitor and bendamustine are not administered simultaneously. In some embodiments, the HDAC inhibitor is administered before bendamustine. In other embodiments, bendamustine is administered before the HDAC inhibitor. The time difference in non-simultaneous administrations can be greater than 2 minutes, five minutes, 10 minutes, 15 minutes, 30 minutes, 45 minutes, 60 minutes, two hours, three hours, six hours, nine hours, 12 hours, 24 hours, 36 hours, or 48 hours. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and bendamustine are administered in a therapeutically effective amount or dosage. A "therapeutically effective amount" is an amount of HDAC6 inhibitor (a compound of Formula I or II) or bendamustine that, when administered to a patient by itself, effectively treats the lymphoma. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC inhibitor and bendamustine are administered in a sub-therapeutically effective amount or dosage. A sub-therapeutically effective amount is an amount of HDAC inhibitor (a compound of Formula I or II) or bendamustine that, when administered to a patient by itself, does not completely inhibit over time the biological activity of the intended target.

Whether administered in therapeutic or sub-therapeutic amounts, the combination of the HDAC inhibitor and bendamustine should be effective in treating lymphoma. For example, a sub-therapeutic amount of bendamustine can be an effective amount if, when combined with a compound of Formula I or II (HDAC inhibitor), the combination is effective in the treatment of lymphoma.

In some embodiments, the combination of compounds exhibits a synergistic effect (i.e., greater than additive effect) in the treatment of the lymphoma. The term "synergistic effect" refers to the action of two agents, such as, for example, a HDAC inhibitor and bendamustine, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments (see, e.g., Example 5) can be predictive of the effect in other species, and animal models exist may be used to further quantify a synergistic effect. The results of such studies can also be used to predict effective dose ratio ranges and the absolute doses and plasma concentrations.

In an embodiment of the combinations provided herein, the molar ratio of the HDAC inhibitor or a pharmaceutically acceptable salt thereof to bendamustine or a pharmaceutically salt thereof, administered to the patient is about 1:100 to about 1:1. For example, the molar ratio can be about 1:100, about 1:95, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:15, about 1:10, about 1:8, about 1:6, about 1:5, about 1:4, about 1:3, about 1:2, or about 1:1. In certain embodiments, the molar ratio is about 1:50 to about 1:2. In other embodiments, the molar ratio is about 1:20 to about 1:2. In further embodiments, the molar ratio is about 1:10 to about 1:2. In yet other embodiments, the molar ratio is about 1:5.

In different embodiments, depending on the combination and the effective amounts used, the combination of compounds can inhibit cancer growth, achieve cancer stasis, or even achieve substantial or complete cancer regression. While the amounts of a HDAC inhibitor and bendamustine should result in the effective treatment of lymphoma, the amounts, when combined, are preferably not excessively toxic to the patient (i.e., the amounts are preferably within toxicity limits as established by medical guidelines). In some embodiments, either to prevent excessive toxicity or provide a more efficacious treatment of lymphoma, a limitation on the total administered dosage is provided. Typically, the amounts considered herein are per day; however, half-day and two-day or three-day cycles also are considered herein. The optimum ratios, individual and combined dosages, and concentrations of the combination partners (an HDAC inhibitor such as Compound A and bendamustine, or a pharmaceutically acceptable salt thereof) of the combination of the invention that yield efficacy without toxicity are based on the kinetics of the therapeutic agents' availability to target sites, and are determined using methods known to those of skill in the art.

Different dosage regimens may be used to treat lymphoma. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day. In some embodiments, each dosage contains both an HDAC inhibitor and bendamustine to be delivered as a single dosage, while in other embodiments, each dosage contains either a HDAC inhibitor and bendamustine to be delivered as separate dosages.

Compounds of bendamustine and Formulas I and II, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and bendamustine of the pharmaceutical combination can be administered in a single unit dose or separate dosage forms. Accordingly, the phrase "pharmaceutical combination" includes a combination of two drugs in either a single dosage form or a separate dosage forms, i.e., the pharmaceutically acceptable carriers and excipients described throughout the application can be combined with an HDAC inhibitor and bendamustine in a single unit dose, as well as individually combined with a HDAC inhibitor and bendamustine when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or bendamustine described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed., (Mack Publishing Company, Easton, Pa., 1990).

Methods of Treatment

The invention relates to methods for treating lymphoma in a subject in need thereof comprising administering to the subject a pharmaceutical combination of the invention. Thus, provided herein are methods for treating lymphoma in a subject in need thereof comprising administering to the subject a therapeutically effective amount of a combination comprising an HDAC inhibitor and bendamustine.

The subject considered herein is typically a human. However, the subject can be any mammal for which treatment is desired. Thus, the methods described herein can be applied to both human and veterinary applications.

The terms "treating" or "treatment" indicates that the method has, at the least, mitigated abnormal cellular proliferation. For example, the method can reduce the rate of lymphoma growth in a patient, or prevent the continued growth or spread of the lymphoma, or even reduce the overall reach of the lymphoma. Within the meaning of the present disclosure, the term "treat" also denotes to arrest, delay the onset (i.e., the period prior to clinical manifestation of a disease) and/or reduce the risk of developing or worsening a disease. The term "prevent", "preventing" or "prevention" as used herein comprises the prevention of at least one symptom associated with or caused by the state, disease or disorder being prevented.

In an embodiment, provided herein is a method for treating lymphoma in a subject in need thereof comprising administering to the subject a therapeutically effective amount of a compound of Formula I or a pharmaceutically acceptable salt thereof, and a therapeutically effective amount of bendamustine or a pharmaceutically acceptable salt thereof.

In a further embodiment, provided herein is a method for treating lymphoma in a subject in need thereof comprising administering to the subject a therapeutically effective amount of Compound A or a pharmaceutically acceptable salt thereof, and a therapeutically effective amount of bendamustine, or a pharmaceutically acceptable salt thereof.

In another embodiment is a method for treating lymphoma in a subject in need thereof comprising administering to the subject a therapeutically effective amount of Compound B or a pharmaceutically acceptable salt thereof, and a therapeutically effective amount of bendamustine or a pharmaceutically acceptable salt thereof.

In an embodiment, provided herein is a method for treating lymphoma in a subject in need thereof comprising administering to the subject a therapeutically effective amount of a compound of Formula II, or a pharmaceutically acceptable salt thereof, and a therapeutically effective amount of bendamustine or a pharmaceutically acceptable salt thereof.

In a further embodiment, provided herein is a method for treating lymphoma in a subject in need thereof comprising administering to the subject a therapeutically effective amount of Compound C or a pharmaceutically acceptable salt thereof, and a therapeutically effective amount of bendamustine or a pharmaceutically acceptable salt thereof.

In a further embodiment, provided herein is a method for treating lymphoma in a subject in need thereof comprising administering to the subject a therapeutically effective amount of Compound D or a pharmaceutically acceptable salt thereof, and a therapeutically effective amount of bendamustine or a pharmaceutically acceptable salt thereof.

In some embodiments, the combination of an HDAC inhibitor or a pharmaceutically acceptable salt thereof, and bendamustine or a pharmaceutically acceptable salt thereof, achieves a synergistic effect in the treatment of the subject in need thereof.

In a further embodiment, the therapeutically effective amount of the combination therapy (i.e., an HDAC inhibitor and bendamustine) comprises the HDAC inhibitor or a pharmaceutically acceptable salt thereof and bendamustine or a pharmaceutically acceptable salt thereof in a synergistic ratio having a combination index (CI) of less than 1.

Thus, in an embodiment, provided herein is a method for treating lymphoma in a subject in need thereof comprising administering to the subject a therapeutically effective amount of Compound A or a pharmaceutically acceptable salt thereof, and a therapeutically effective amount of bendamustine or a pharmaceutically acceptable salt thereof, wherein Compound A or a pharmaceutically acceptable salt thereof, and bendamustine or a pharmaceutically acceptable salt thereof, are administered in a synergistic ratio having a combination index of less than 1.

Another embodiment of the invention includes a method for inducing apoptosis of a cancer cell comprising administering to the cell a combination comprising an HDAC inhibitor or a pharmaceutically acceptable salt thereof and bendamustine or a pharmaceutically acceptable salt thereof. In some embodiments, the induction of apoptosis is associated with an increase in reactive oxygen species. In some embodiments, the apoptosis is associated with the activation of caspase 3, caspase 9, caspase 8, and/or PARP.

Yet another embodiment of the invention includes a method for reducing the viability of a cancer cell comprising administering to the cell a combination comprising an HDAC inhibitor or a pharmaceutically acceptable salt thereof and bendamustine or a pharmaceutically acceptable salt thereof.

Still another embodiment of the invention includes a method for reducing clonogenic survival of a cancer cell comprising administering to the cell a combination comprising an HDAC inhibitor or a pharmaceutically acceptable salt thereof and bendamustine or a pharmaceutically acceptable salt thereof.

A further embodiment of the invention includes a method for suppressing cell proliferation in a cancer cell comprising administering to the cell a combination comprising an HDAC inhibitor or a pharmaceutically acceptable salt thereof and bendamustine or a pharmaceutically acceptable salt thereof.

Another embodiment of the invention includes a method for reducing the expression of Bcl-2 in a cancer cell comprising administering to the cell a combination comprising an HDAC inhibitor or a pharmaceutically acceptable salt thereof and bendamustine or a pharmaceutically acceptable salt thereof.

Another embodiment of the invention includes a method for increasing expression of the cell cycle proteins p21 and p27, and decreasing expression of the cell cycle protein cyclin D in a cancer cell comprising administering to the cell a combination comprising an HDAC inhibitor or a pharmaceutically acceptable salt thereof and bendamustine or a pharmaceutically acceptable salt thereof.

Another embodiment of the invention includes a method for inducing dephosphorylation of PI3K/Akt signalling pathways in a cancer cell comprising administering to the cell a combination comprising an HDAC inhibitor or a pharmaceutically acceptable salt thereof and bendamustine or a pharmaceutically acceptable salt thereof.

Another embodiment of the invention includes a method for enhancing microtubule stability in a cancer cell comprising administering to the cell a combination comprising an HDAC inhibitor or a pharmaceutically acceptable salt thereof and bendamustine or a pharmaceutically acceptable salt thereof.

Another embodiment of the invention includes a method for down-modulating IL-10 expression in a cancer cell comprising administering to the cell a combination comprising an HDAC inhibitor or a pharmaceutically acceptable salt thereof and bendamustine or a pharmaceutically acceptable salt thereof.

In another aspect, provided herein is a method for treating a solid tumor in a subject in need thereof comprising administering to the subject a therapeutically effective amount of a combination comprising an HDAC inhibitor or a pharmaceutically acceptable salt thereof and bendamustine or a pharmaceutically acceptable salt thereof. In an embodiment, the tumor type is responsive to treatment with bendamustine as a single agent. Non-limiting examples of these tumors include metastatic breast cancer, small-cell lung cancer, refractory soft tissue sarcoma, and relapsed or refractory germ cell cancer.

Kits

In other embodiments, kits are provided. Kits according to the invention include package(s) comprising compounds or compositions of the invention. In some embodiments, kits comprise a HDAC inhibitor, or a pharmaceutically acceptable salt thereof, and bendamustine or a pharmaceutically acceptable salt thereof.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the invention to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substitutents, derivatives, formulations or methods of the invention may be made without departing from the spirit of the invention and the scope of the appended claims. Definitions of the variables in the structures in the schemes herein are commensurate with those of corresponding positions in the formulae presented herein.

The synthesis of the compounds of Formula I is provided in PCT/US2011/021982, which is incorporated herein by reference in its entirety. The synthesis of compounds of Formula II is provided in PCT/US2011/060791, which is incorporated herein by reference in its entirety.

Example 1: Synthesis of 2-(diphenylamino)-N-(7-(hydroxyamino)-7-oxoheptyl)pyrimidine-5-carboxamide (Compound A)

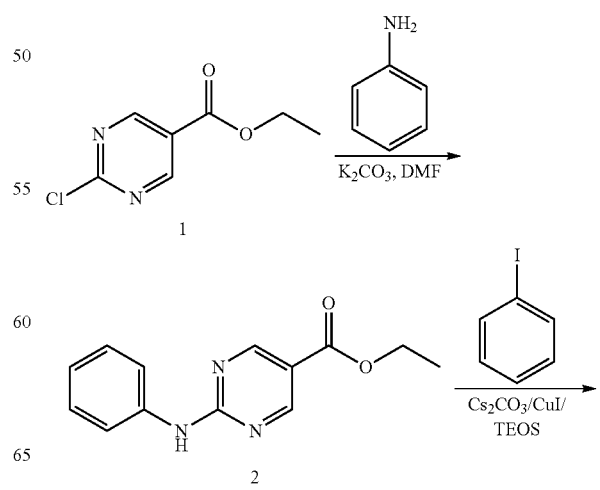

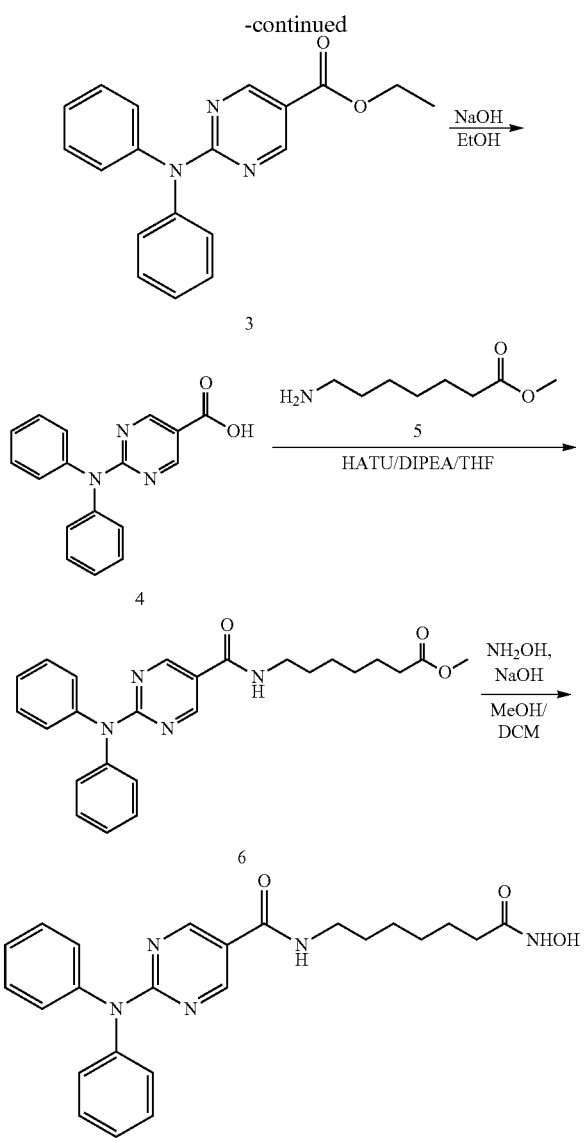

Synthesis of Intermediate 2

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

A mixture of the compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 h. After cooling to rt, the residue was diluted with EtOAc (200 ml) and 95% EtOH (200 ml), $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at rt for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at rt overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (ricolinostat or Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at rt for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-((2-chlorophenyl)(phenyl)amino)-N-(7-(hydroxyamino)-7-oxoheptyl)pyrimidine-5-carboxamide (Compound B)

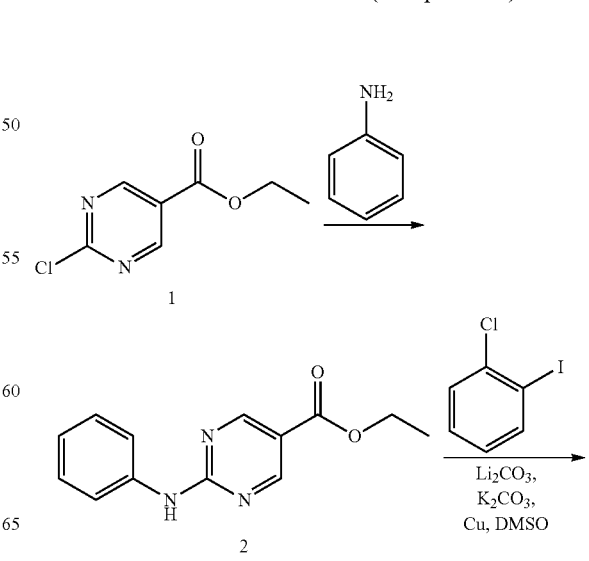

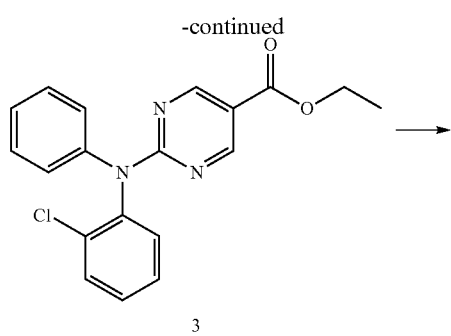

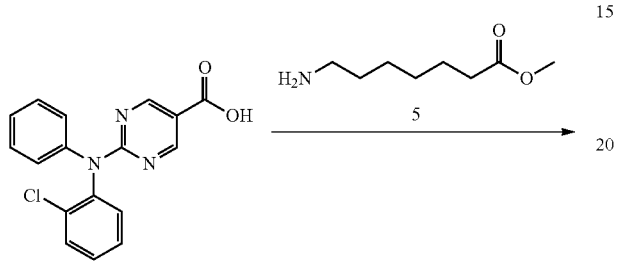

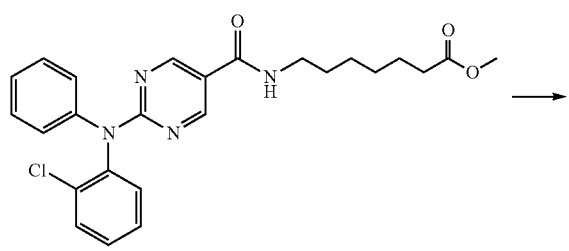

Compound B

Synthesis of Intermediate 2

See synthesis of intermediate 2 in Example 1.

Synthesis of Intermediate 3

A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 µm) in DMSO (690 ml) was degassed and purged with nitrogen. The resulting mixture was stirred at 140° C. Work-up of the reaction gave compound 3 at 93% yield.

Synthesis of Intermediate 4

See synthesis of intermediate 4 in Example 1.

Synthesis of Intermediate 6

See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B)

See synthesis of Compound A in Example 1.

Example 3: Synthesis of 2-((1-(3-fluorophenyl)cyclohexyl)amino)-N-hydroxypyrimidine-5-carboxamide (Compound C)

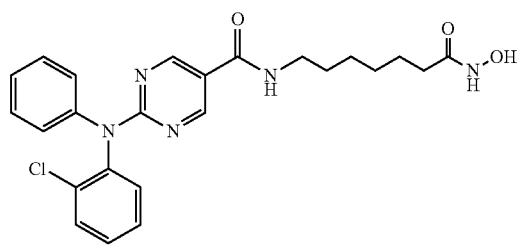

Synthesis of 1-(3-fluorophenyl)cyclohexanecarbonitrile

To a solution of 2-(3-fluorophenyl)acetonitrile (100 g, 0.74 mol) in Dry DMF (1000 ml) was added 1,5-dibromopentane (170 g, 0.74 mol), NaH (65 g, 2.2 eq) was added dropwise at ice bath. After addition, the resulting mixture was vigorously stirred overnight at 50° C. The suspension was quenched by ice water carefully, extracted with ethyl acetate (3*500 ml). The combined organic solution was concentrate to afford the crude which was purified on flash column to give 1-(3-fluorophenyl)cyclohexanecarbonitrile as pale solid (100 g, 67%).

Synthesis of 1-(3-fluorophenyl)cyclohexanecarboxamide

To a solution of 1-(3-fluorophenyl)cyclohexanecarbonitrile (100 g, 0.49 mol) in PPA (500 ml) was heated at 110° C. for about 5-6 hours. After completed, the resulting mixture was carefully basified with sat.NaHCO3 solution until the PH=8-9. The precipitate was collected and washed with water (1000 ml) to afford 1-(3-fluorophenyl)cyclohexanecarboxamide as white solid (95 g, 87%).

Synthesis of 1-(3-fluorophenyl)cyclohexanamine

To a solution of 1-(3-fluorophenyl)cyclohexanecarboxamide (95 g, 0.43 mol) in n-BuOH (800 ml) was added NaClO (260 ml, 1.4 eq), then 3N NaOH (400 ml, 2.8 eq) was added at 0° C. and the reaction was stirred overnight at r.t. The resulting mixture was extracted with EA (2*500 ml), the combined organic solution was washed with brine, dried to afford the crude which was further purification on treating with HCl salt as white powder (72 g, 73%).

Synthesis of ethyl 2-(1-(3-fluorophenyl)cyclohexylamino)pyrimidine-5-carboxylate To a solution of 1-(3-fluorophenyl)cyclohexanamine hydrochloride (2.29 g 10 mmol) in Dioxane (50 ml) was added ethyl 2-chloropyrimidine-5-carboxylate (1.87 g, 1.0 eq) and DIPEA (2.58 g, 2.0 eq). The mixture was heated overnight at 110-120° C. The resulting mixture was directly purified on silica gel column to afford the coupled product as white solid (1.37 g, 40%).

Synthesis of 2-((1-(3-fluorophenyl)cyclohexyl)amino)-N-hydroxypyrimidine-5-carboxamide (Compound C)

To a solution of ethyl 2-(1-(3-fluorophenyl)cyclohexylamino)pyrimidine-5-carboxylate (100 mg, 0.29 mmol) in MeOH/DCM (10 ml, 1:1) was added 50% NH2OH in water (2 ml, excess), then sat. NaOH in MeOH (2 ml, excess) was added at 0° C. and the reaction was stirred for 3-4 hours. After completed, the resulting mixture was concentrated and acidified with 2N HCl to the PH=4-5. The precipitate was collected and washed by water (10 ml) to remove the NH2OH and dried to afford 2-((1-(3-fluorophenyl)cyclohexyl)amino)-N-hydroxypyrimidine-5-carboxamide as white powder (70 mg, 73%).

Example 4: Synthesis of N-hydroxy-2-((1-phenylcyclopropyl)amino)pyrimidine-5-carboxamide (Compound D)

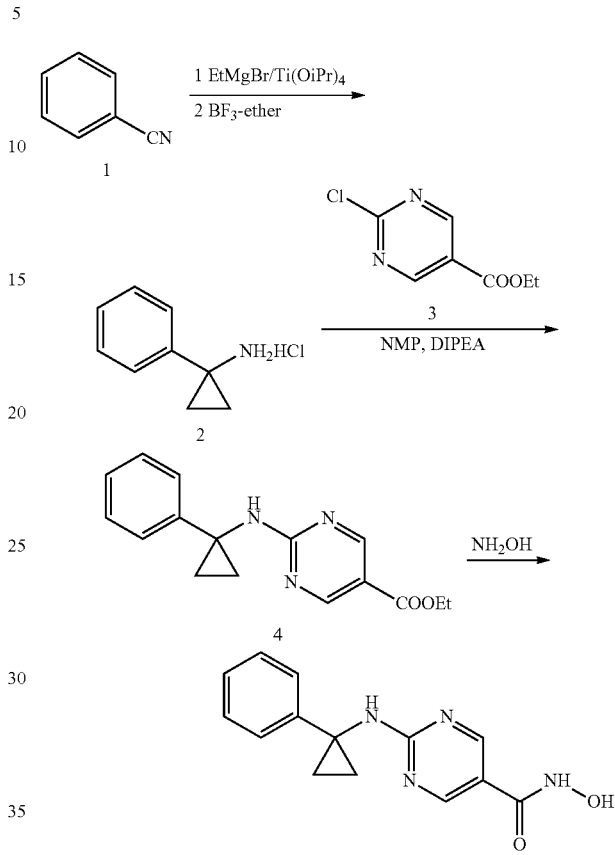

Synthesis of Intermediate 2

A solution of compound 1, benzonitrile, (250 g, 1.0 equiv.), and Ti(OiPr)4 (1330 ml, 1.5 equiv.) in MBTE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF3-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na2SO4 and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4

Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl) amino)pyrimidine-5-carboxamide (Compound D)

A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5: Preclinical Screening of the HDAC6 Inhibitor Ricolinostat (Compound A) Combined with Bendamustine in Lymphoma Cell Lines Histone deacetylase (HDAC) inhibitors are emerging as an exciting new therapeutic option for lymphoid malignancies. Ricolinostat (Compound A) is a novel selective histone deacetylase 6 (HDAC6) inhibitor. HDAC6 is a class IIB histone deacetylase that plays an important role in the cellular response to environmental stress.

The purpose of this study was to evaluate the preclinical activity of the HDAC6 inhibitor ricolinostat alone, and the potential of combining ricolinostat with bendamustine (an alkylating agent) in lymphoma cell lines.

The following methods were used in this study. The anti-tumor activity of ricolinostat was investigated using a panel of six lymphoma cell lines: two follicular lymphoma (FL) (WSU-NHL, RL) cell lines, two mantle cell lymphoma (MCL) (Granta-519, Jeko-1) cell lines, and two T-cell lymphoma (TCL) (HUT-78—cutaneous T cell lymphoma, and Karpas-299—anaplastic lymphoma cells) cell lines. The IC$_{50}$ value of each drug was calculated from curves based on ricolinostat concentrations (0.01-100 µM) and bendamustine (25-300 µM) concentrations after 24, 48, and 72 hours. Cell proliferation was determined by using the CellTiter 96® Aqueous One Solution Cell Proliferation Assay kit, and cell cytotoxicity was determined with the MTT-assay. The interaction between the drugs was evaluated by isobologram analysis based upon the Chou-Talalay method to determine if the combination was additive or synergistic. Clonogenic survival was studied with the methylcellulose clonogenic assay. Apoptosis, reactive oxygen species (ROS), cell cycle analysis, and Bcl-2 protein expression were measured by flow cytometry. Caspase activation and the PI3K/AKT pathway were analyzed by Western blot.

Figure 1B:
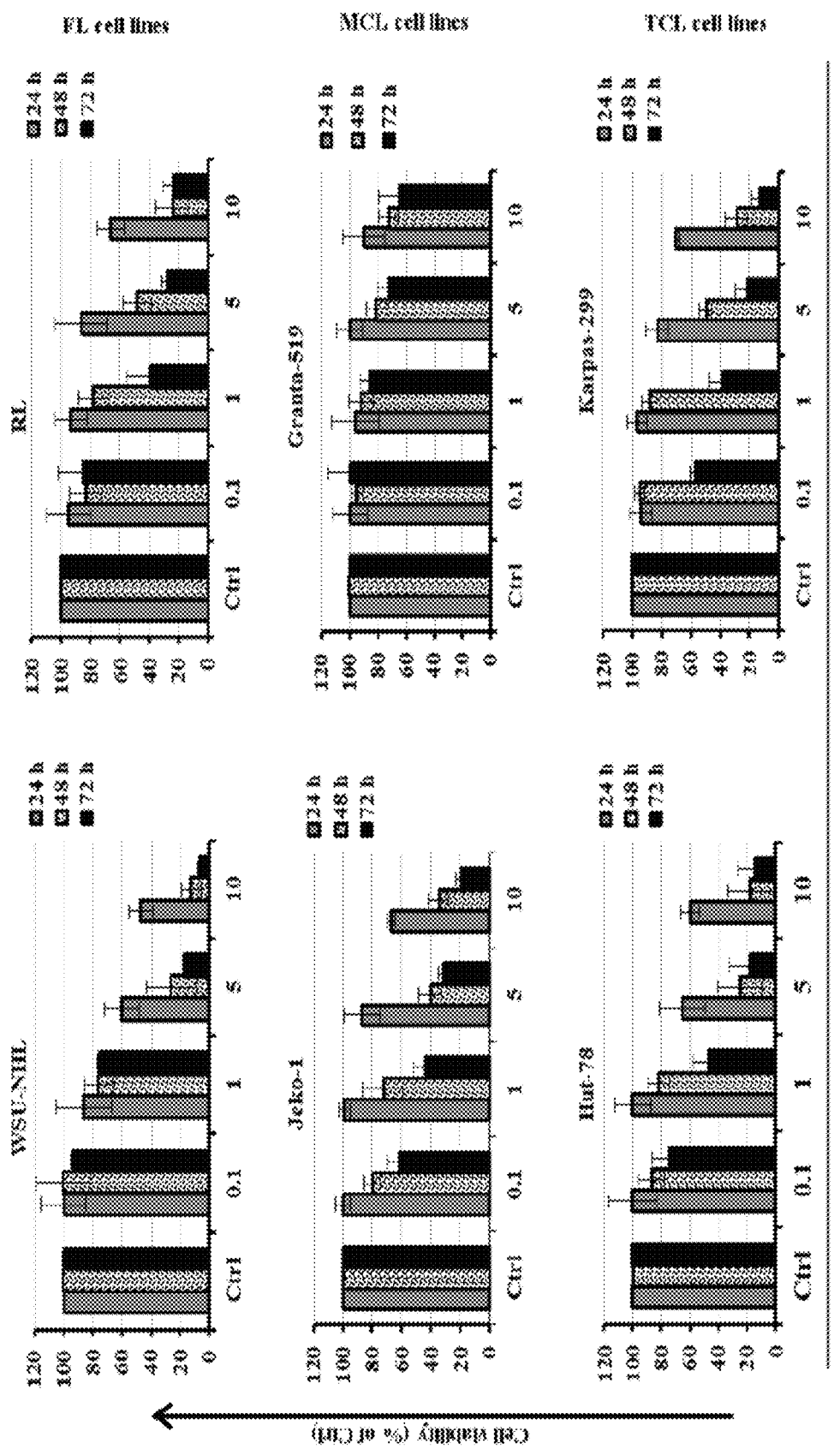
FIG. 1B shows the effect of ricolinostat on cell viability. Ricolinostat induces dose and time dependent manner growth inhibition in a panel of six lymphoma cell lines (WSU-NHL, RL, Granta-519, Jeko-1, Hut-78 and Karpas-299) treated with a serial dosage of ricolinostat (0.1-100 µM) for 24-72 h. Data are representative of at least three independent experiments and represent the mean±SD.

I. Ricolinostat Inhibited Lymphoma Cell Viability:

The anti-tumor activity of ricolinostat was investigated using a panel of six lymphoma cell lines: two follicular lymphoma (FL) (WSU-NHL, RL) cell lines, two mantle cell lymphoma (MCL) (Granta-519, Jeko-1) cell lines, and two T-cell lymphoma (TCL) (HUT-78—cutaneous T cell lymphoma, and Karpas-299—anaplastic lymphoma cells) cell lines. HDAC6 protein is expressed in all cell lines examined (FIG. 1A). Ricolinostat was administered to each cell line at various concentrations (0.01, 0.1, 1, 5, and 10 µM), and cell viability was measured at 24, 48, and 72 hours. FIG. 1B shows the results for the two follicular lymphoma cell lines, the two mantle cell lymphoma cell lines, and the two T-cell lymphoma cell lines. The IC$_{50}$ and CI95% for ricolinostat was measured in each cell line at 24 and 48 hours, as shown in Table 1.

TABLE 1

IC$_{50}$ values for ricolinostat in lymphoma cell lines.
Lymphoma cell lines were treated with ricolinostat at a range
of concentrations from 0.01 to 100 µM for 24 and 48 hours.
IC$_{50}$ values were calculated using MTT assay.
CI 95%: Confidence Interval.
Values represent three independent experiments.

| Lymphoma cell lines | | 24 h | 48 h |
|---|---|---|---|
| Follicular cell lymphoma | WSU-NHL | | |
| | IC$_{50}$ | 8.65 | 1.97 |
| | CI95% | 3.01; 14.3 | 1.01; 4.95 |
| | RL | | |
| | IC$_{50}$ | — | 3.37 |
| | CI95% | — | 7.81; 14.6 |
| Mantle cell lymphoma | Jeko-1 | | |
| | IC$_{50}$ | — | 3.42 |
| | CI95% | — | 1, 64; 8.48 |
| | Granta-519 | | |
| | IC$_{50}$ | 64 | 20 |
| | CI95% | 52; 76 | 13; 26 |
| T-cell lymphoma | Hut-78 | | |
| | IC$_{50}$ | — | 1.51 |
| | CI95% | — | 3.84; 6.86 |
| | Karpas-299 | | |
| | IC$_{50}$ | — | 4.82 |
| | CI95% | — | 0.15; 9.80 |

Ricolinostat inhibited cell viability in a time-dose dependent manner with IC$_{50}$ values ranging from 1.51 to 64 µM. Significant cytotoxic effect was observed after 48 h of treatment in five out of six lymphoma cell lines present in the panel. The most sensitive cell lines were WSU-NHL and Hut-78 (IC$_{50}$: 1.97-1.51 µM) and the less sensitive the mantle cell lymphoma cell lines Granta-519 (IC$_{50}$: 20-64 µM) (FIG. 1B and Table 1).

Figure 1C:
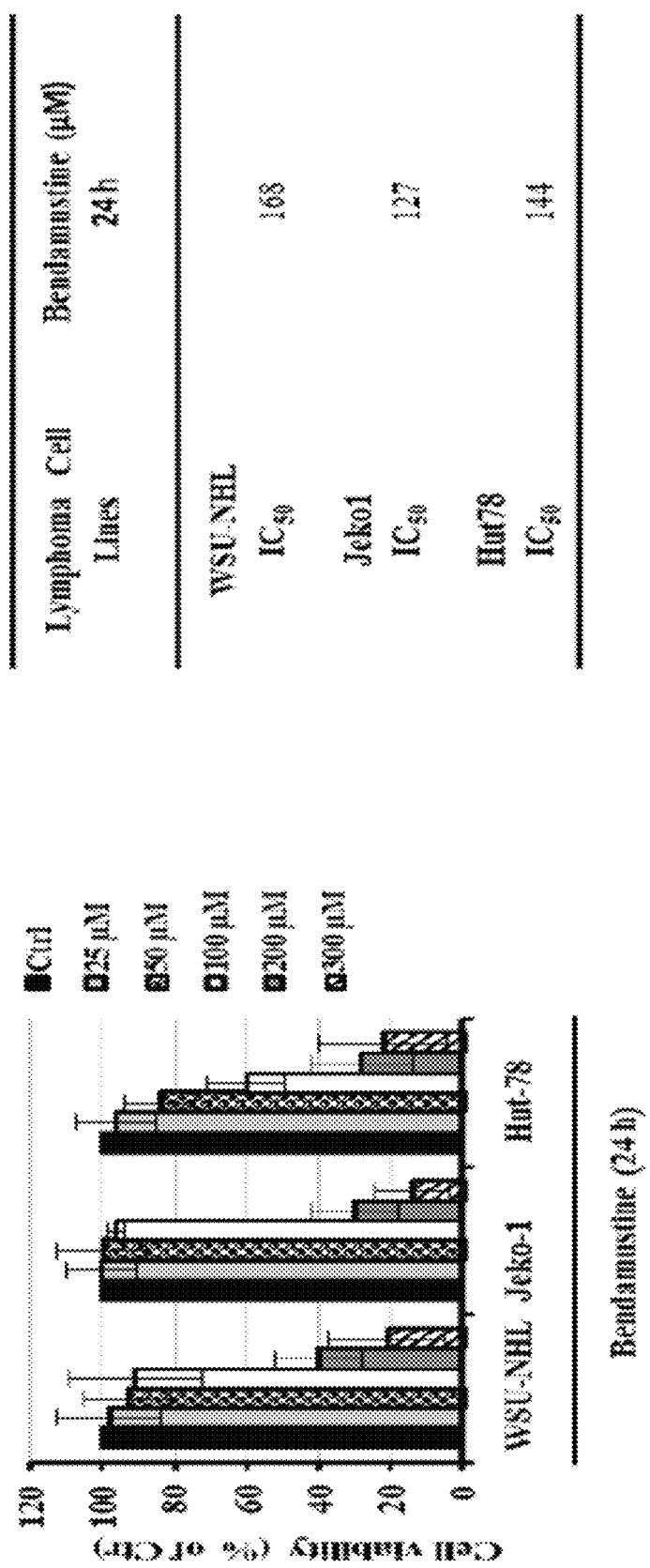
FIG. 1C shows the antiproliferative activity of bendamustine. WSU-NHL, Jeko-1 and Hut-78 cells were treated with bendamustine (25-300 µM) for 24 h. Bendamustine demonstrated a dose-dependent inhibition of cell viability and a range of $IC_{50}$ from 127 µM to 168 µM. Values represent three independent experiments.

II. Growth Inhibition of Bendamustine:

The anti-tumor activity of bendamustine was investigated using a panel of three lymphoma cell lines: a follicular lymphoma (FL) (WSU-NHL) cell line, a mantle cell lymphoma (MCL) (Jeko-1) cell line, and a T-cell lymphoma (TCL) (HUT-78—cutaneous T cell lymphoma) cell line. Bendamustine was administered to each cell line at various concentrations (25, 50, 100, 200, and 300 µM), and cell viability was measured at 24 and 48 hours. FIG. 1C shows the cell viability in each of WSU-NHL, HUT-78, and JEKO-1 cells at 24 hours after administration of various concentrations of bendamustine (25, 50, 100, 200, and 300 µM). The IC$_{50}$ for bendamustine was measured in each cell line at 24 hours, as shown in Table 2.

TABLE 2

| Cell line | IC$_{50}$ at 24 hours |
|---|---|
| WSU-NHL | 168 |
| HUT-78 | 144 |
| JEKO-1 | 127 |

The results in FIG. 1C and Table 2 show that bendamustine (25-300 μM) alone induced time- and dose-dependent inhibition of cell viability in lymphoma cell lines.

III. Ricolinostat/Bendamustine Inhibited Cell Viability in a Synergistic Manner.

Figure 2A:
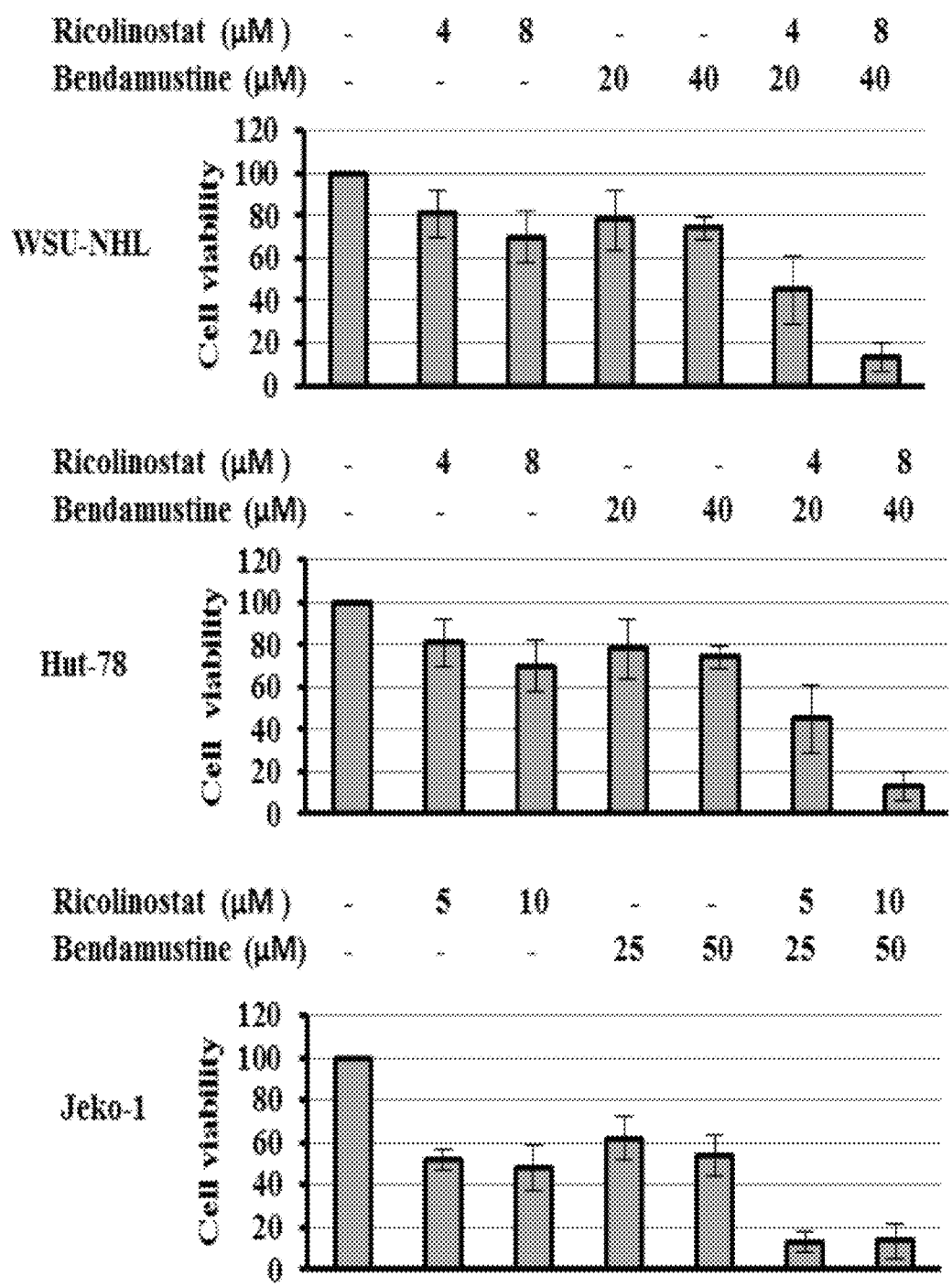
FIG. 2A shows the synergistic effect of drug combination on cell viability of WSU-NHL, Hut-78 and Jeko-1 cells. Cells were treated with different concentrations of ricolinostat (0, 2, 2.5, 4, 5, 8 and 10 µM) in combination with bendamustine (0, 10, 20, 25, 40, 50 and 100 µM) and was assayed by MTT at 24 h.
Figure 2B:
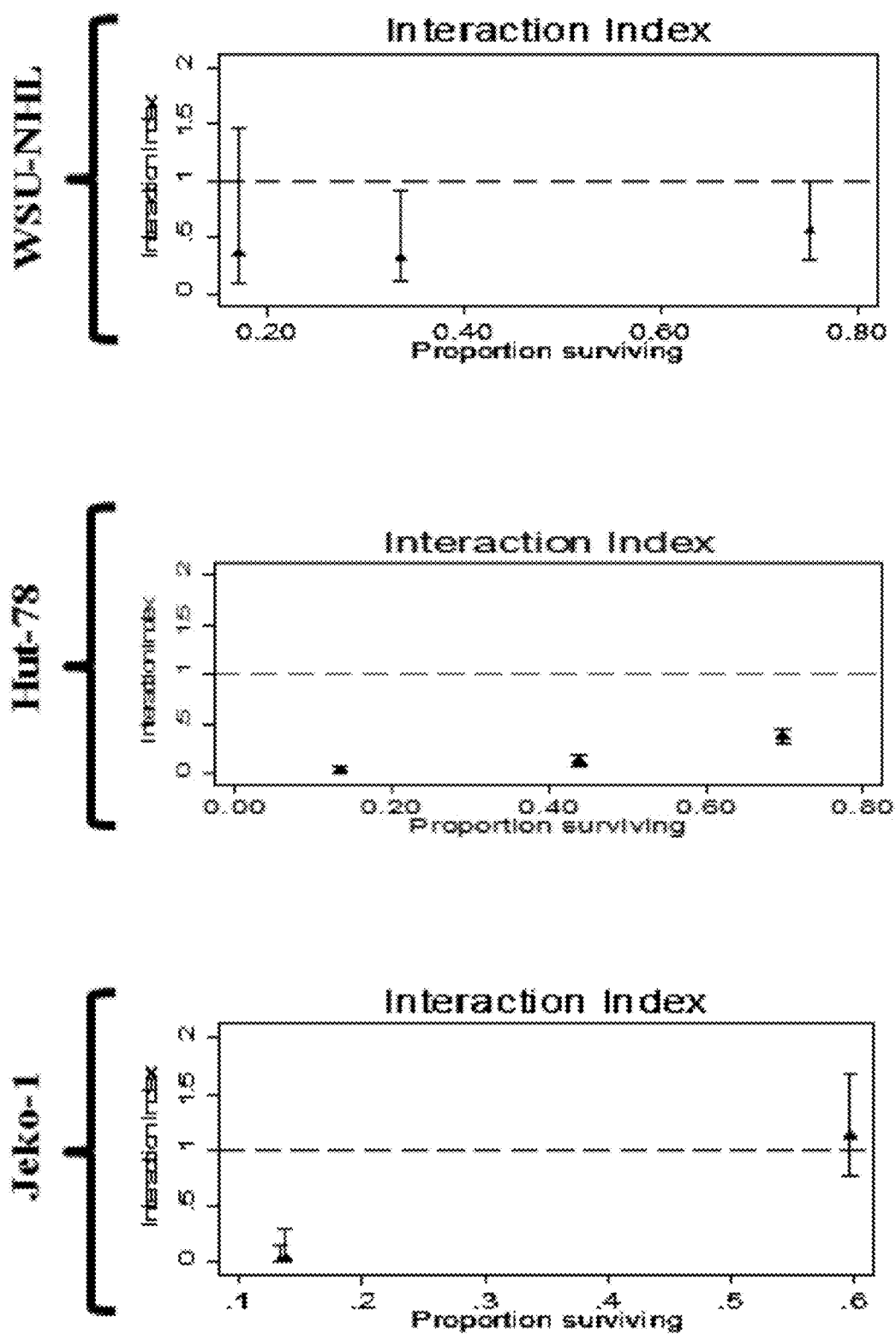
FIG. 2B shows confirmation of the synergistic effect shown in FIG. 2A via isobologram analysis (interaction index <1).
Figure 2C:
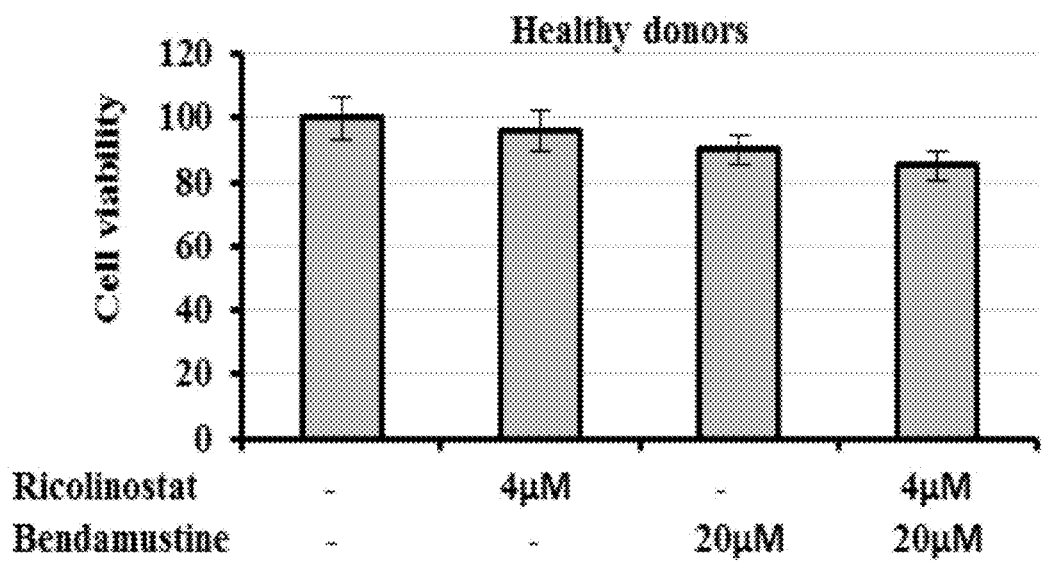
FIG. 2C shows the cell viability of freshly isolated PBMCs from three healthy subjects cultured with ricolinostat (4 µM) and bendamustine (20 µM) alone and in combination, for 24 h.

The interaction between the drugs (ricolinostat and bendamustine) was evaluated by isobologram analysis based upon the Chou-Talalay method to determine if the combination was additive or synergistic. The most sensitive three lymphoma cell lines of the panel (WSU-NHL, Hut-78 and Jeko-1) were treated with increasing concentrations of ricolinostat (0, 2, 2.5, 4, 5, 8, 10 μM) in combination with bendamustine (0, 10, 20, 25, 40, 50, 100 μM). The drug combination induced a significantly stronger cytotoxic effect in all cell lines tested. The effect of the drugs on each cell line was determined, and the combination index (CI) was measured. A CI<1 means synergy; a CI=1 means an additive effect; and a CI>1 means antagonism. Ricolinostat (2, 4, 8 μM) and bendamustine (10, 20, 40 μM) showed a synergistic interaction with a combination index (CI) ranging between 0.027 and 0.553 in WSU-NHL and Hut-78 cells respectively. Ricolinostat (5, 10 μM) with bendamustine (50, 100 μM) showed a CI of 0.02 and 0.04 in Jeko-1 cells (FIGS. 2A and 2B, Table 3). No interference on cell viability was observed in normal PBMNCs (FIG. 2C). The synergistic effect (CI<1) was observed at the dose of 4 μM of ricolinostat and 20 μM of bendamustine in WSU-NHL and Hut-78 cells and 5 μM of ricolinostat and 50 μM bendamustine in Jeko-1 at 24 h.

Importantly, the drug combination did not trigger a relevant decrease in the viability of normal peripheral blood mononuclear cells (FIG. 2C).

TABLE 3

Isobologram analysis of combination of Ricolinostat with Bendamustine.

| | Ricolinostat (μM) | Bendamustine (μM) | Effect | CI (CI95%) |
|---|---|---|---|---|
| WSU-NHL | 2 | 10 | 0.75 | 0.553 (0.307-0.996) |
| | 4 | 20 | 0.34 | 0.324 (0.116-0.900) |
| | 8 | 40 | 0.17 | 0.305 (0.091-1.46) |
| Hut-78 | 2 | 10 | 0.70 | 0.374 (0.313-0.446) |
| | 4 | 20 | 0.44 | 0.124 (0.079-0.193) |
| | 8 | 40 | 0.13 | 0.027 (0.011-0.067) |
| Jeko-1 | 2.5 | 25 | 59.6 | 1.13 (0.77-1.67) |
| | 5 | 50 | 13.3 | 0.04 (0.01-0.15) |
| | 10 | 100 | 13.7 | 0.02 (0.01-0.31) |

IV. Ricolinostat Alone and in Combination Reduces Clonogenic Survival and Overcomes the Protective Effect of BM-MSCs.

Figure 2D:
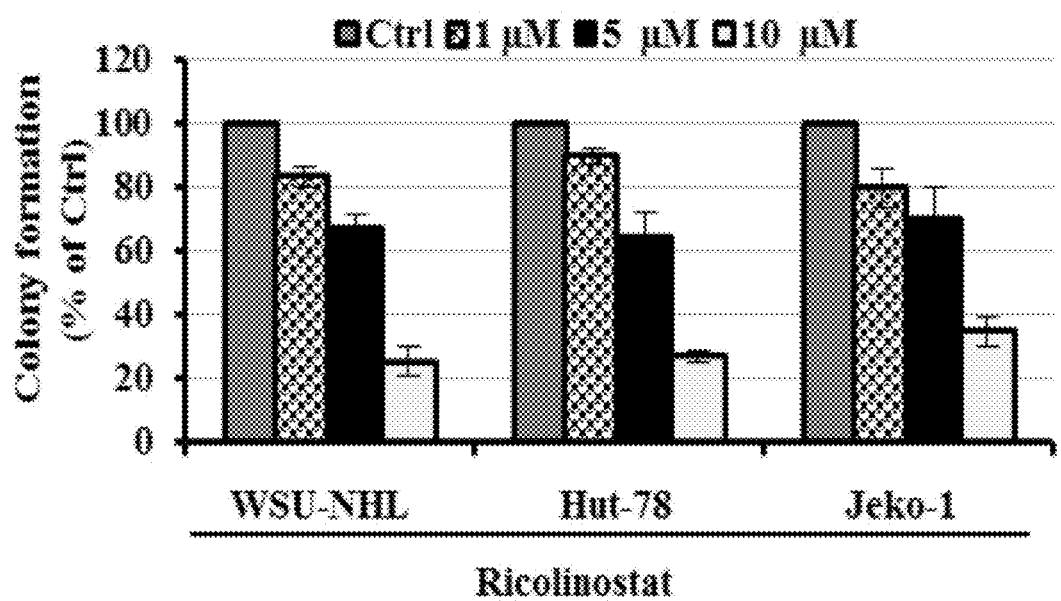
FIG. 2D and FIG. 2E show effects of ricolinostat alone and in combination with bendamustine on clonogenic survival. WSU-NHL, Hut-78 and Jeko-1 cells were first incubated with ricolinostat alone (1, 5, 10 µM) (C) and subsequently in combination with bendamustine (D) in liquid culture for 24 h. Treated cells were incubated in methylcellulose and colonies consisting of more 50 cell were counted after 10 days. The relative percentage with respect to control cells are shown and represent the mean±SD of three separate experiments.
Figure 2E:
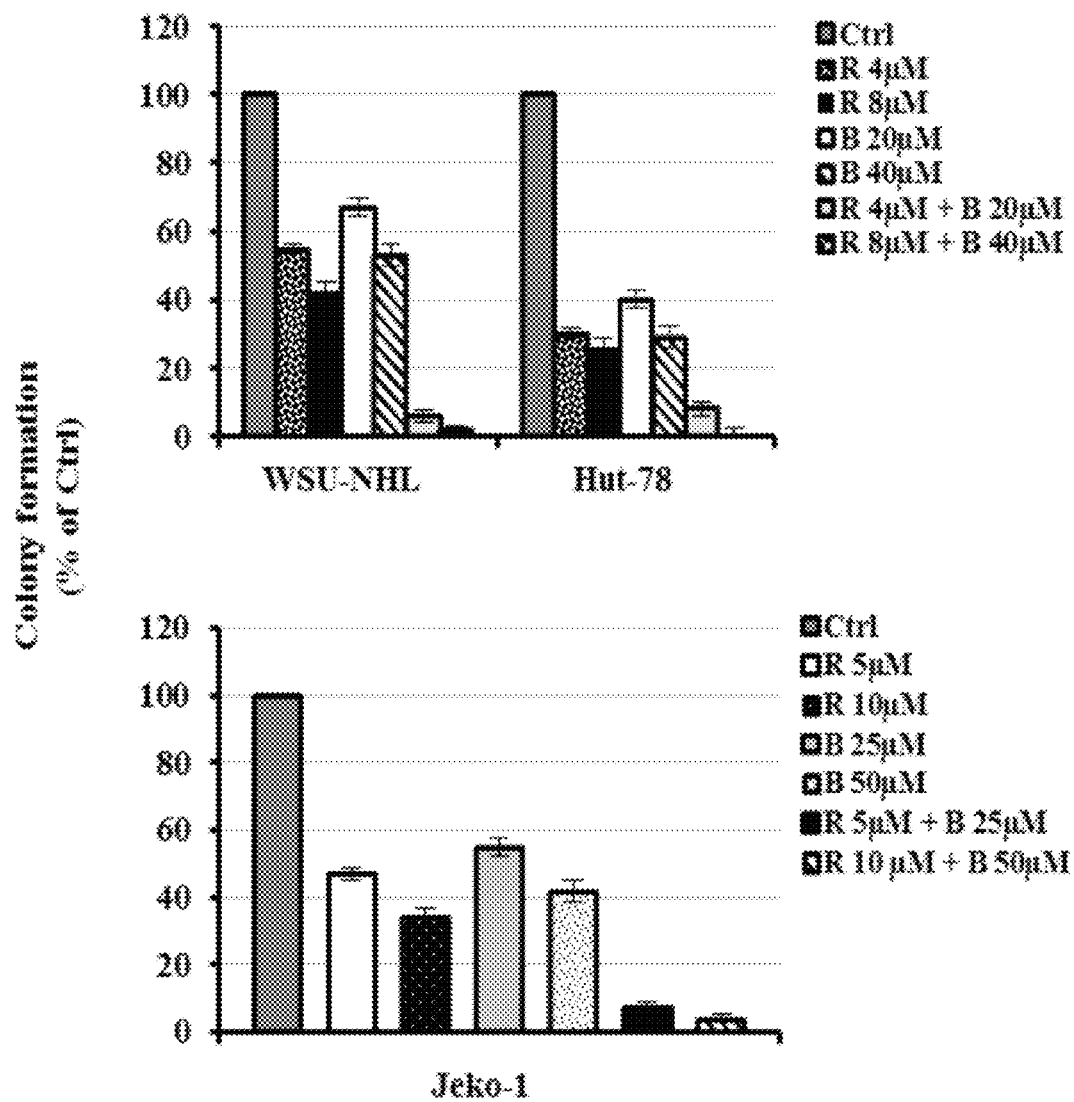
Figure 3A:
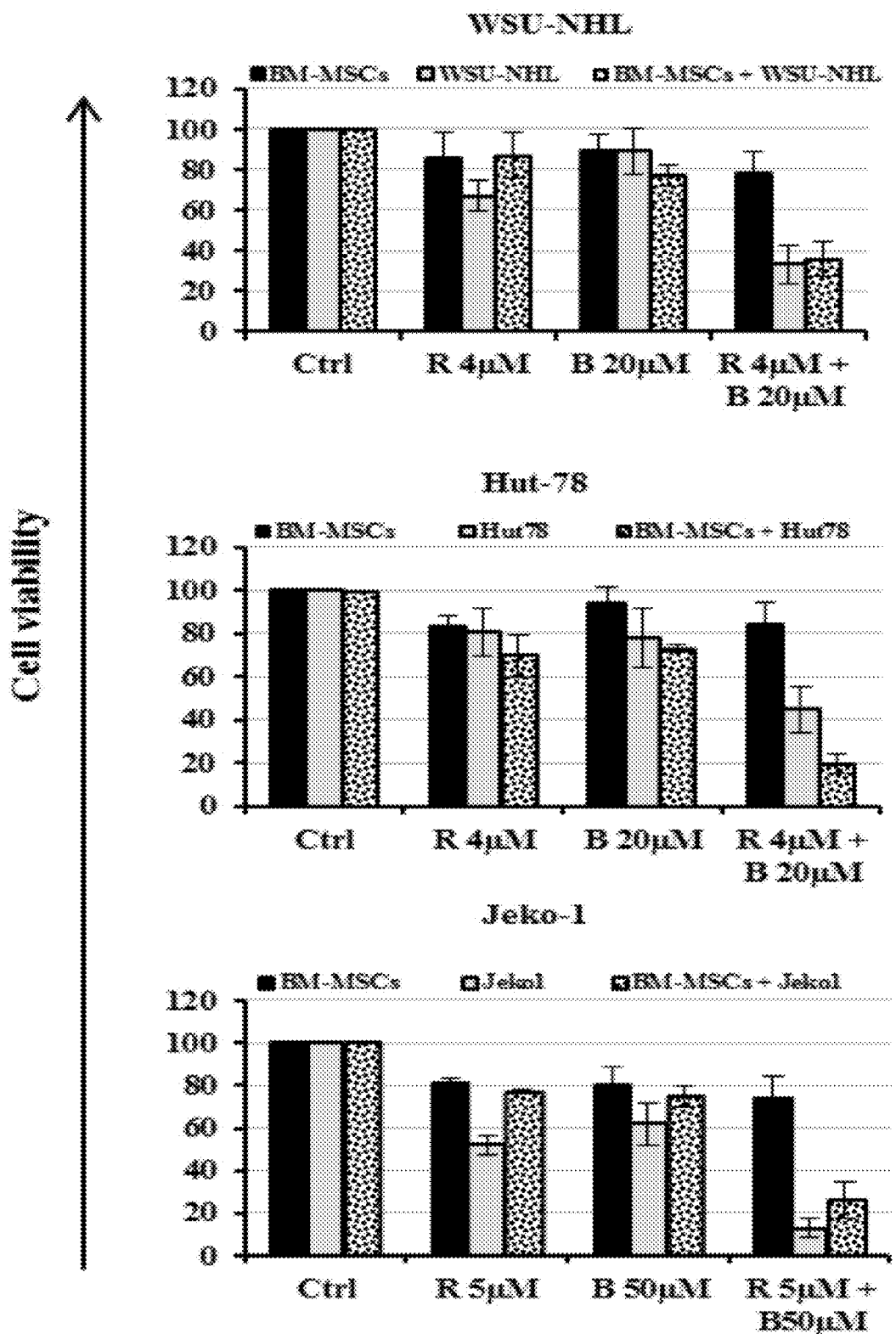
FIG. 3A shows that ricolinostat and bendamustine overcomes the protective effect of BM-MSCs. Cell viability of WSU-NHL, Hut-78 and Jeko-1 cells co-cultured with or without BM-MSCs and exposed to ricolinostat (R) and bendamustine (B) alone and in combination for 24 h. The drug combination suppressed cell viability of lymphoma cell lines when co-cultured with BM-MSCs. All data are expressed as a percentage of untreated control±SD of triplicate culture.

Ricolinostat reduced clonogenic survival in a dose dependent manner (FIG. 2D) as a single agent. Ricolinostat/bendamustine induced a significant inhibition of the colony formation compared with the single agents (FIG. 2E). Drug combination decreased the cell viability of lymphoma cells co-cultured with BM-MSCs, indicating that it overcomes the anti-apoptotic effects conferred by the bone marrow microenvironment and the combination had minimal or no cytotoxic effect on BMSCs (FIG. 3A).

V. Ricolinostat/Bendamustine Affected the Cell Cycle Through the Regulatory Proteins p21 and p27.

Figure 3B:
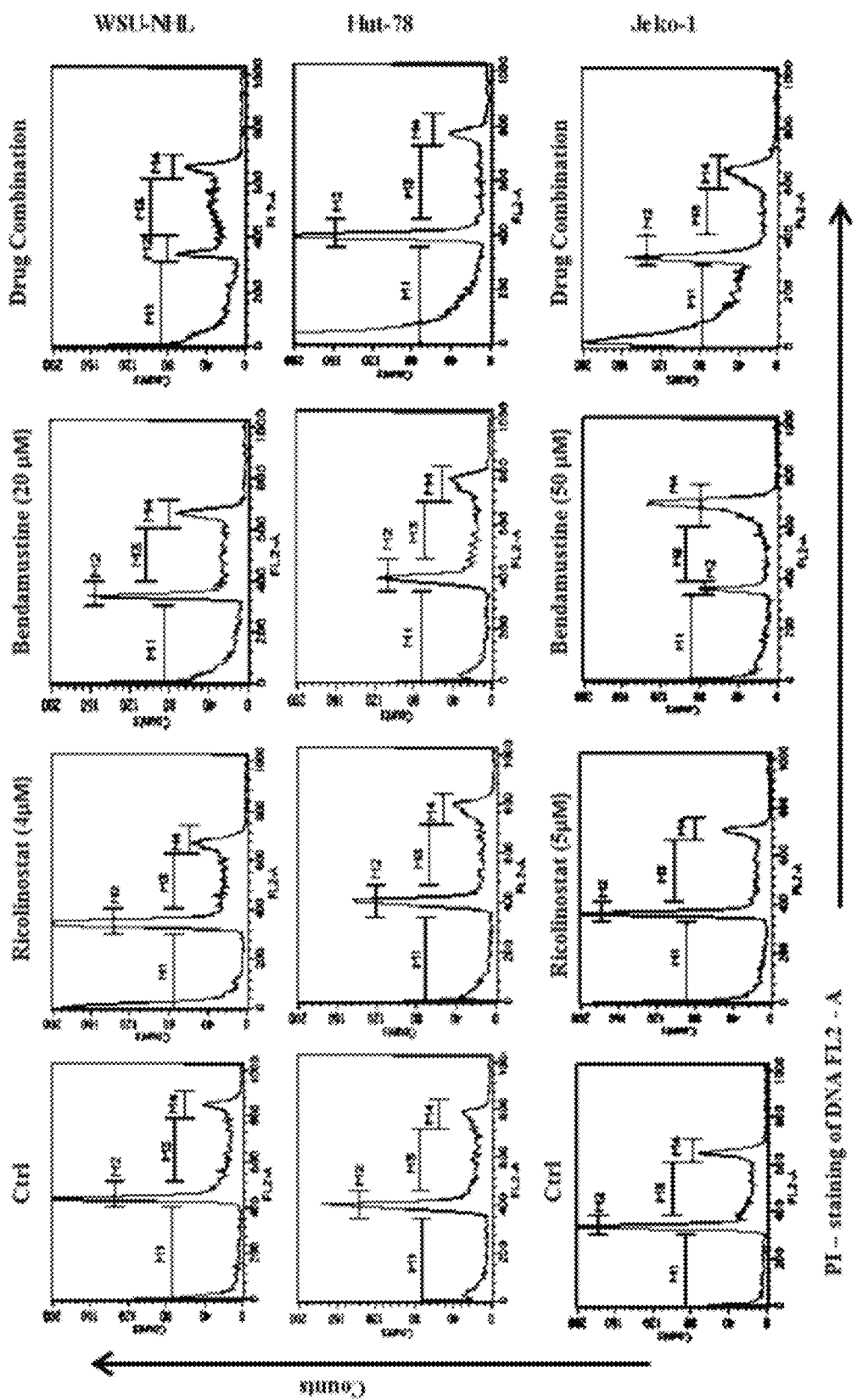
FIG. 3B shows the effect of drug combination on cell cycle profile of WSU-NHL, Hut-78, treated with ricolinostat (4 µM) and bendamustine (20 µM) alone and in combination and Jeko-1 cells treated with ricolinostat (5 µM) and bendamustine (50 µM) alone and in combination. The bars of M1, M2, M3 and M4 indicate the sub-$G_0/G_1$, $G_0/G_1$, S and $G_2/M$ phases, respectively.
Figure 3C:
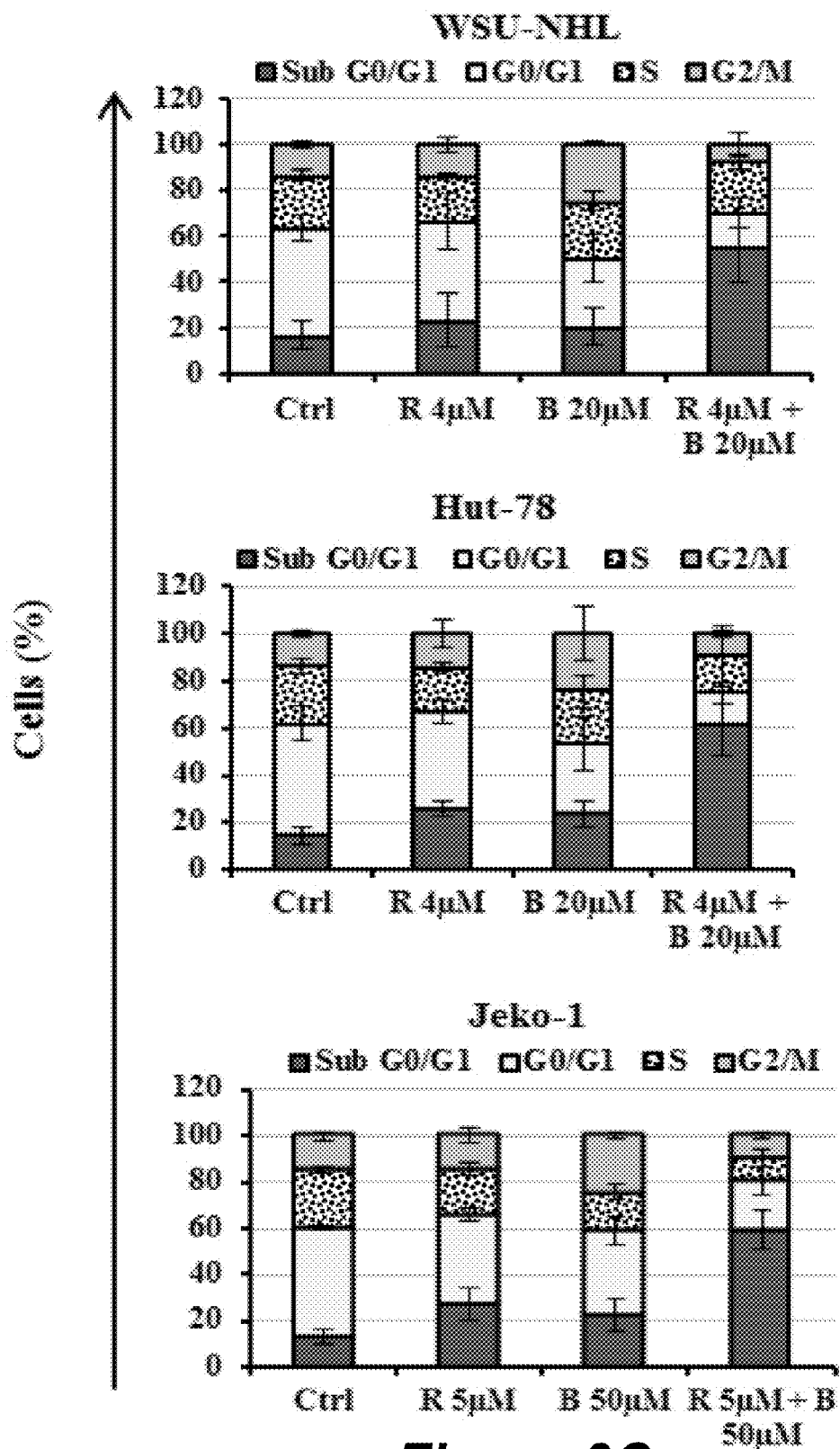
FIG. 3C shows the percentage of cell cycle distribution of lymphoma cell lines in different phases after 24 hours of treatment. All values represent the mean±SD of three independent experiments.
Figure 4:
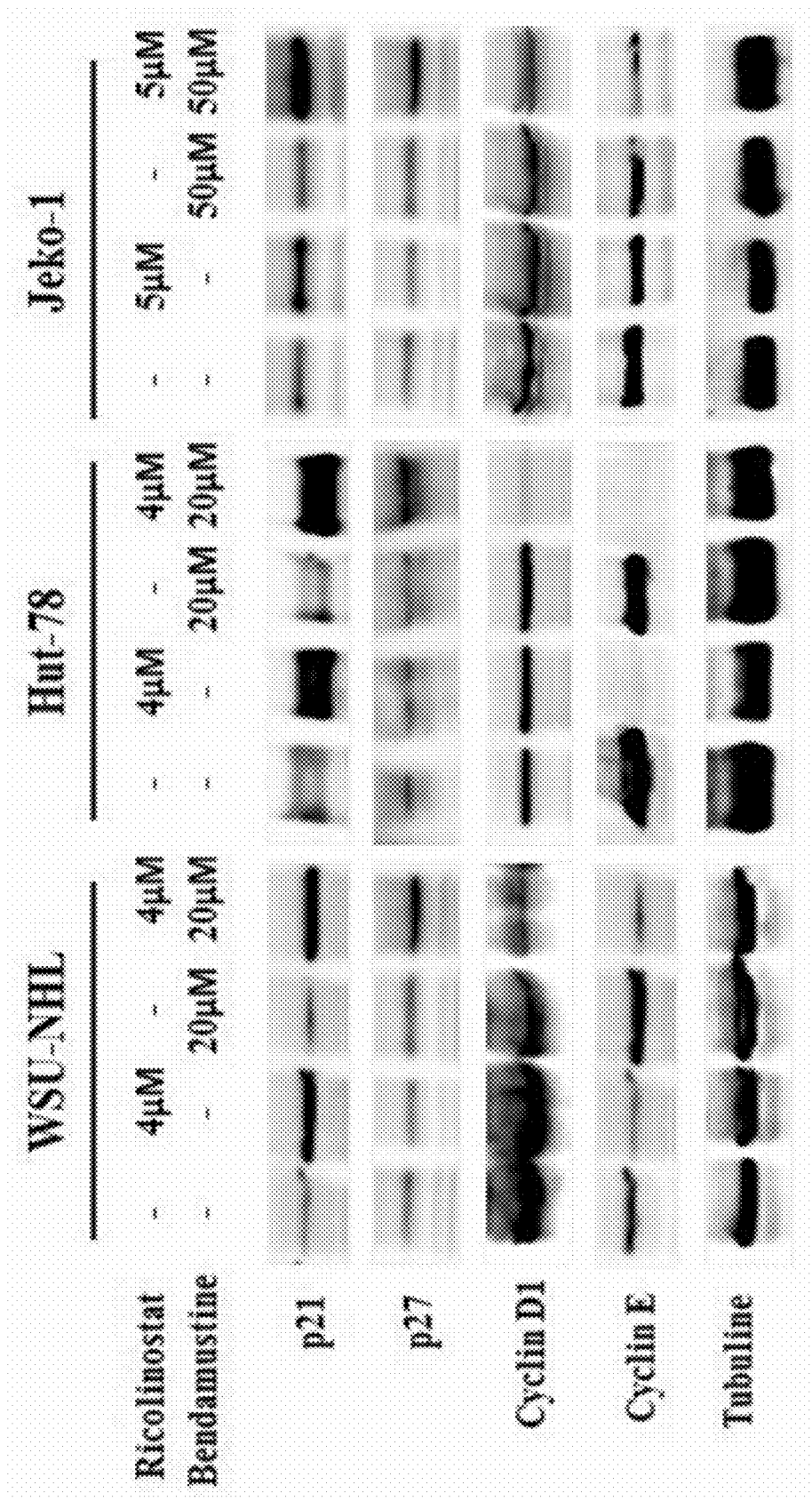
FIG. 4 shows the effect of ricolinostat/bendamustine on regulatory proteins of cell cycle. WSU-NHL, Hut-78 were treated with 4 µM of ricolinostat and 20 µM of bendamustine alone and in combination; Jeko-1 were treated with 5 µM of ricolinostat and 50 µM of bendamustine alone and in combination. Western blots were performed after 24 h of treatment. Tubulin was used to normalize protein loading.

Ricolinostat induced an increase in the percentage of cells in the $G_0/G_1$ phase and a decrease in the $G_2/M$ phase of the cell cycle compared with untreated control in all cell lines tested, and the drug combination reduced the proportion of cells in the $G_0/G_1$ and S phases and caused an increase of "sub-$G_0/G_1$" peak (FIGS. 3B and 3C). The treatment with drug combination for 24 h caused a decrease of cyclin D1, and cyclin E in lymphoma cells and the level of p21 protein and p27 increased (FIG. 4) confirming the observations on cell cycle.

VI. The Drug Combination Induced Apoptosis and Activated ER Stress Through ROS Generation.

Figure 5A:
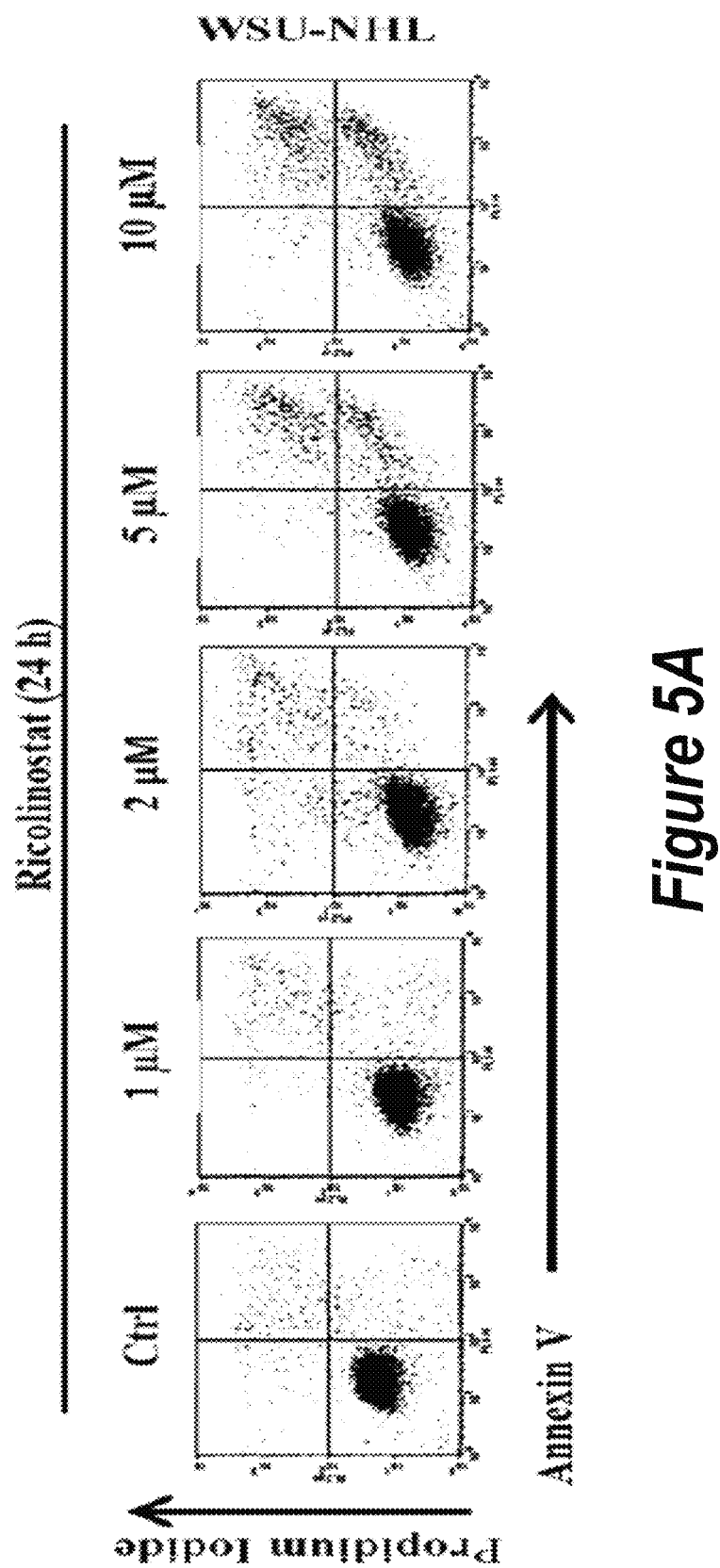
FIGS. 5A-5E show the effect of ricolinostat alone and in combination with bendamustine on apoptosis.
Figure 5B:
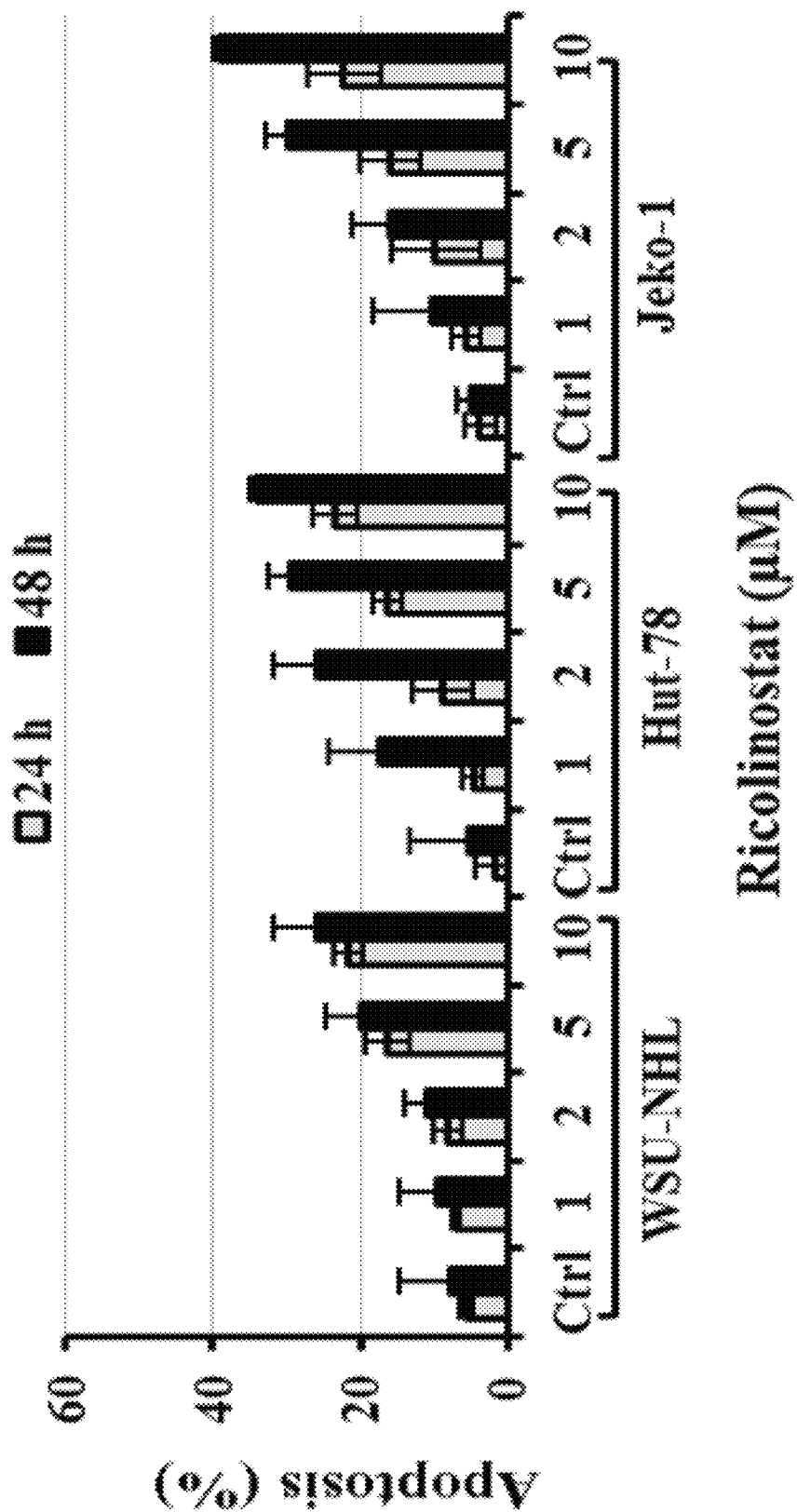
Figure 5C:
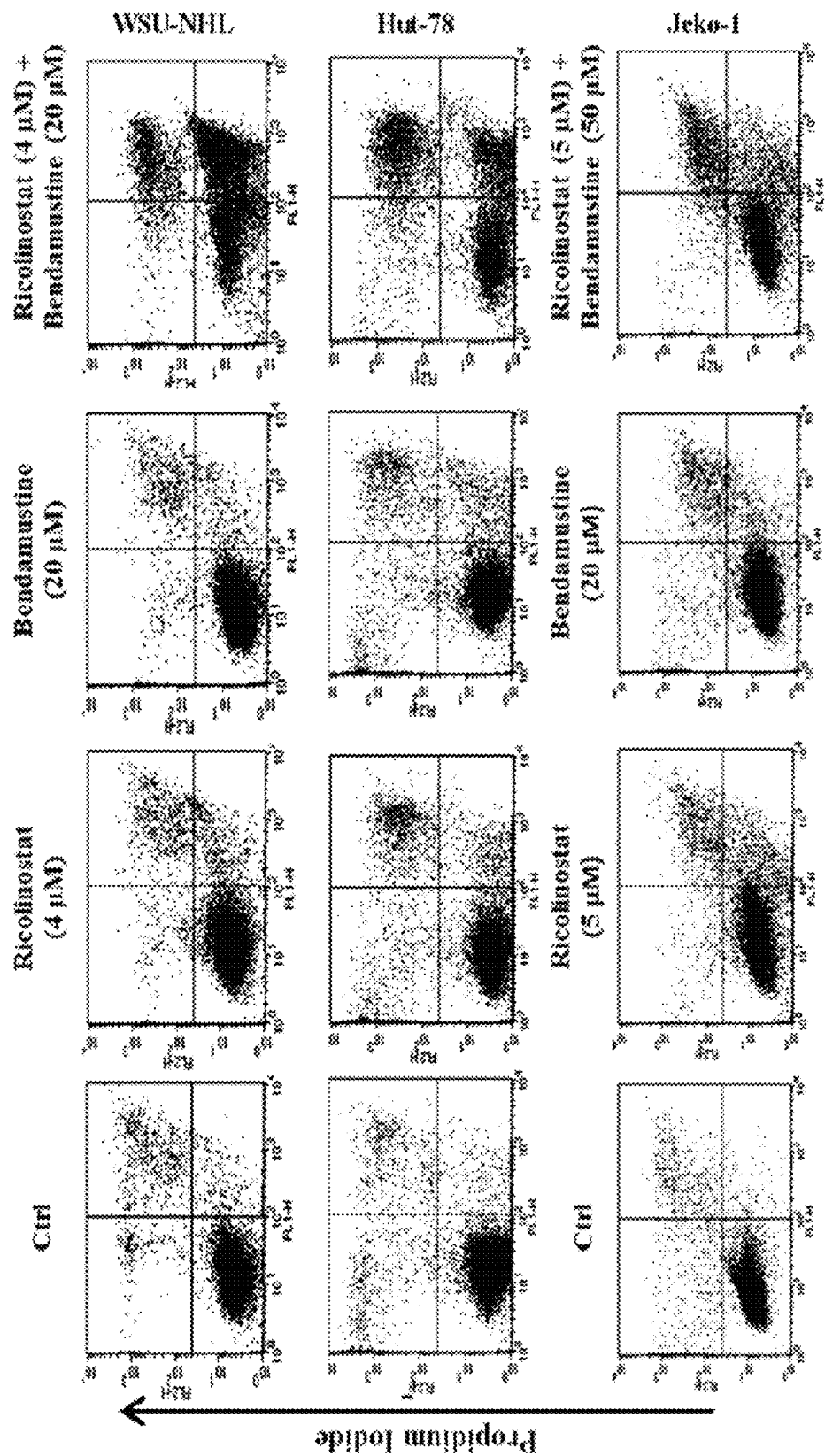
Figure 5D:
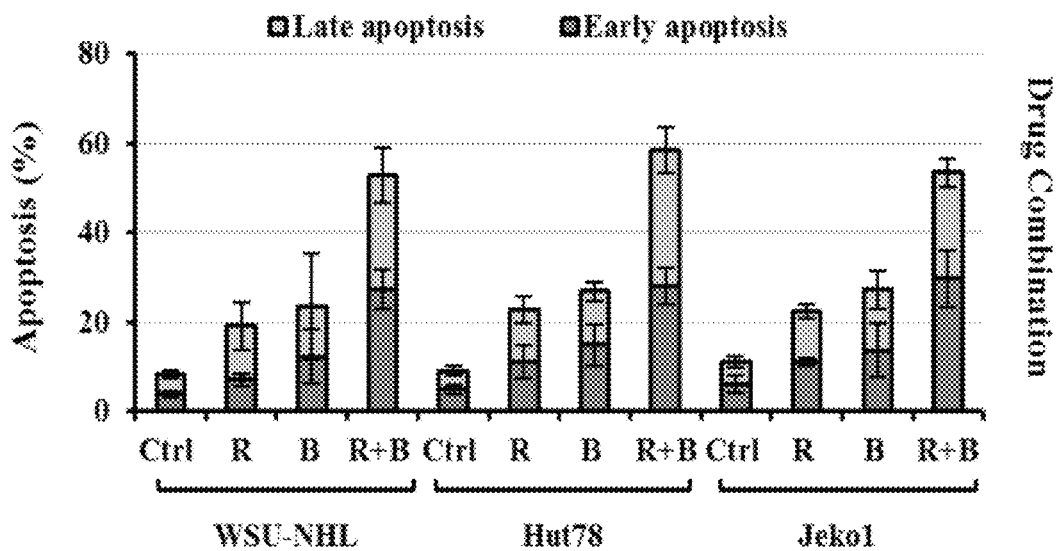

Ricolinostat (1-10 μM) induced apoptosis in all cell lines examined in time- and dose dependent manner as measured by flow cytometry (FIGS. 5A and 5B). In FIG. 5A WSU-NHL cells were treated with either ricolinostat, bendamustine, or ricolinostat and bendamustine at the indicated concentrations. After 24 hours, the cells were fixed and stained with propidium iodide, and were analyzed by flow cytometry. FIG. 5B shows the percentage of apoptosis after 24 hours in each of the WSU-NHL, HUT-78, and Jeko-1 cell lines after administration of the indicated concentrations of either ricolinostat (R), bendamustine (B), or ricolinostat (R) and bendamustine (B). The results in FIGS. 5A-E show that ricolinostat in combination with bendamustine induced apoptosis at 24 hours. This effect was enhanced by the combination with bendamustine (FIGS. 5C and 5D).

Figure 5E:
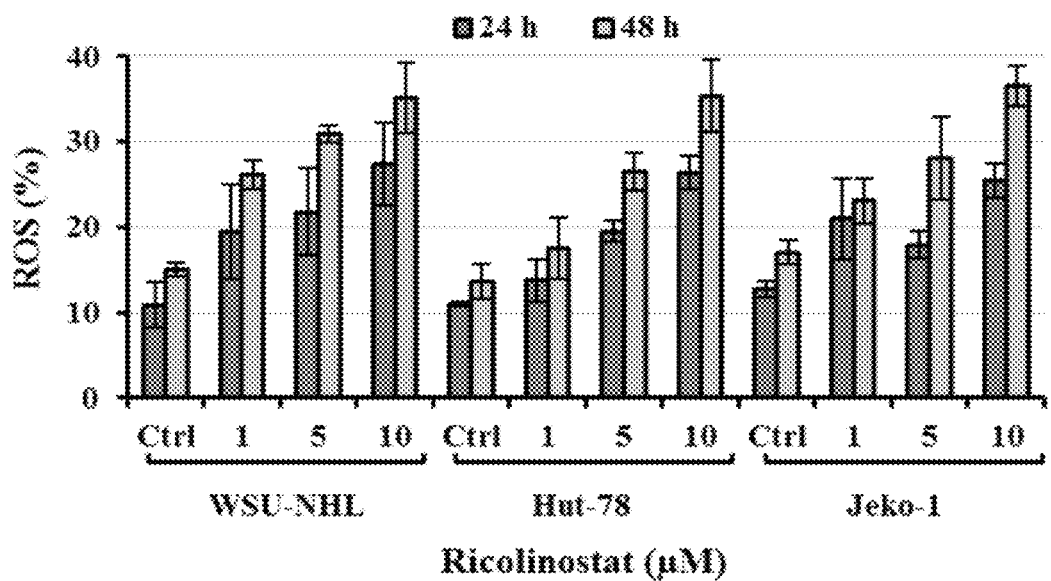
Figure 6A:
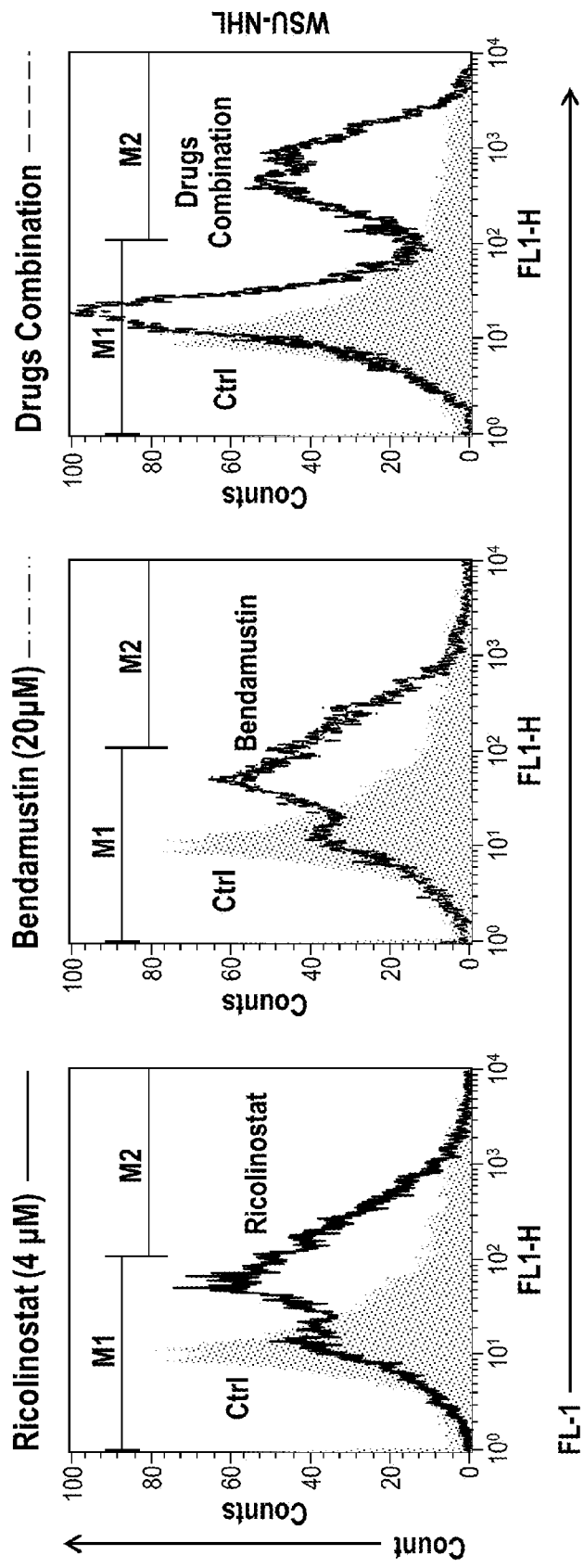
FIGS. 6A-6D show that the drug combination causes ROS generation with a strong effect at 24 h.
Figure 6B:
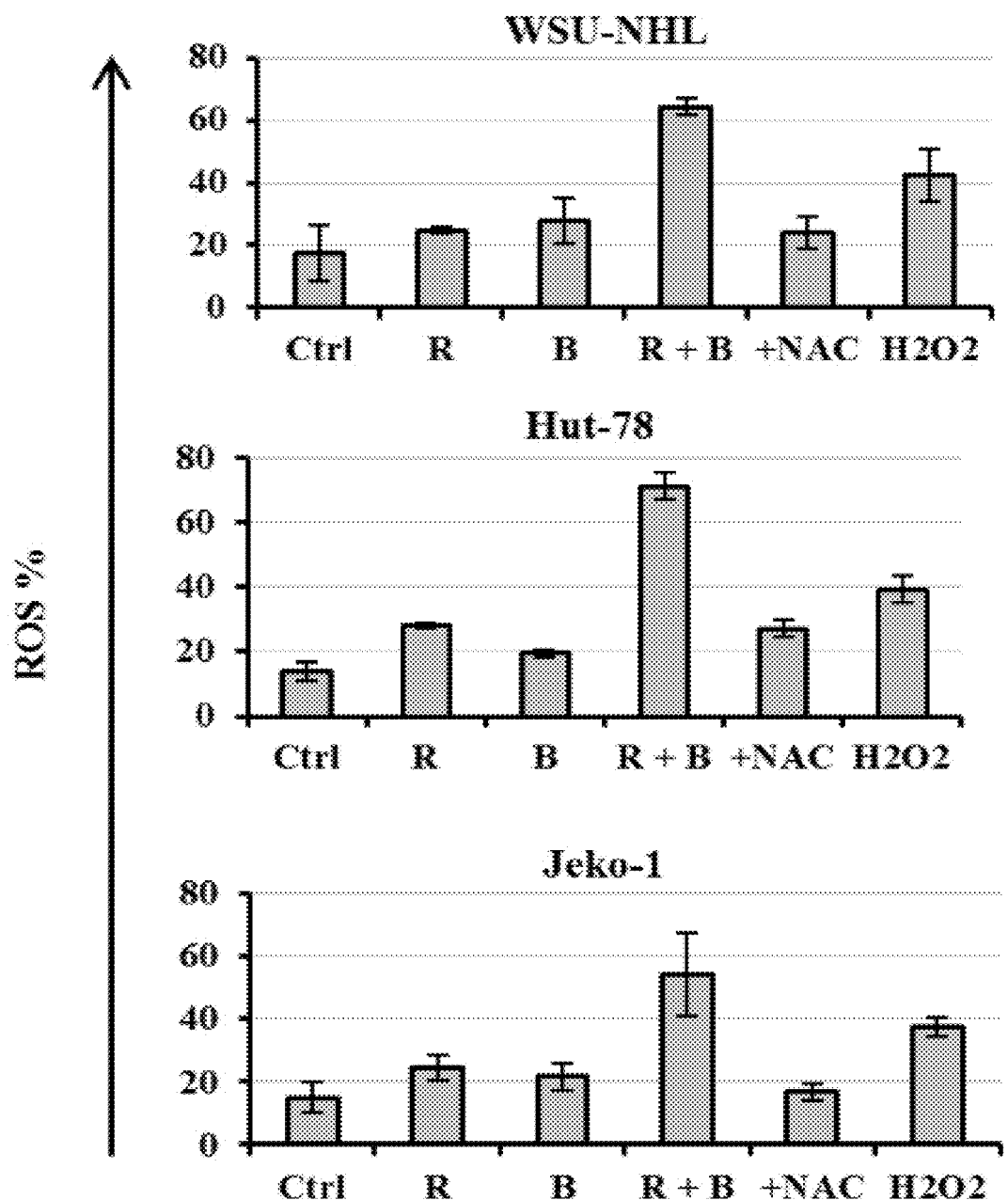
Figure 6C:
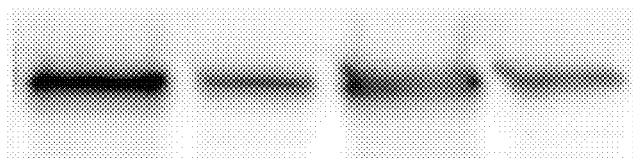
Figure 6C:
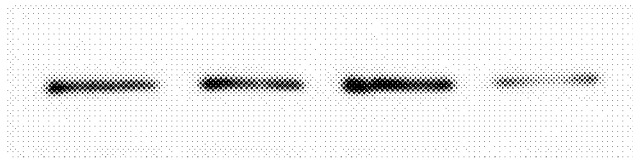
Figure 6C:
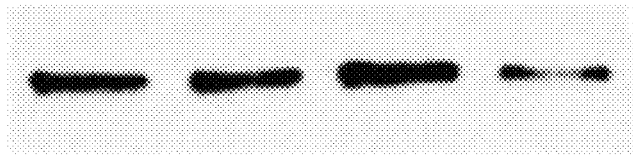
Figure 6C:
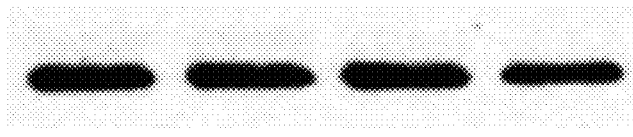
Figure 6D:
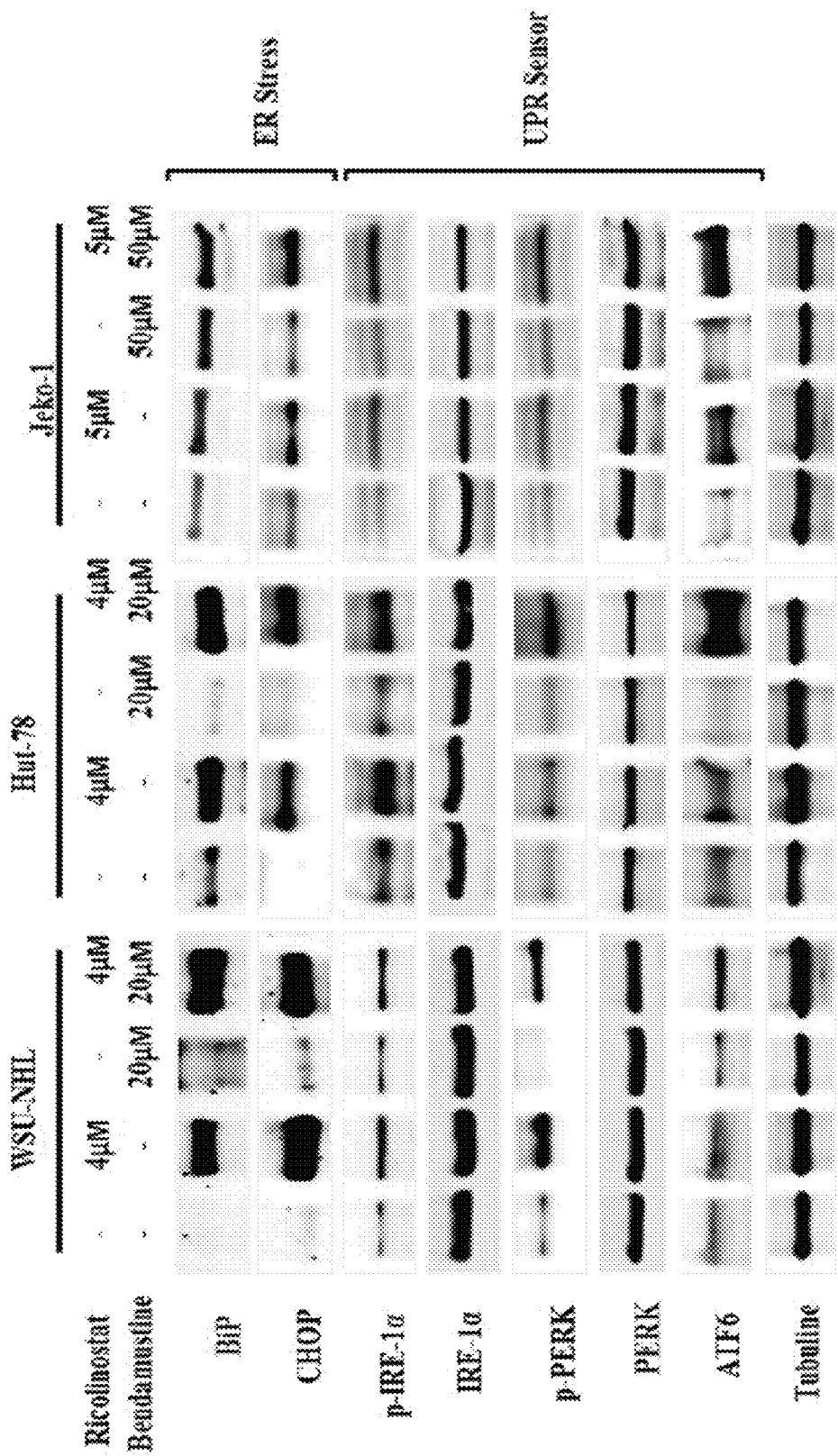

Ricolinostat alone (1, 5, 10 μM) induced an increase of ROS production at 24 h, which further increased after 48 h (FIG. 5E). Ricolinostat/bendamustine induced a significant increase of ROS-positive cells when compared with single agents and the co-administration of the antioxidant NAC, a ROS scavenger, reduced the generation of ROS (FIGS. 6A and 6B). ROS generation induced by the drug combination was associated with a decrease of Thioredoxin-1 (Trx1) expression (FIG. 6C). The possible modification of the protein expression levels of some hallmarks of ER stress such as BIP and CHOP and the expression of UPR sensors including IRE1, ATF6 and PERK were analyzed. As showed in FIG. 6D, the ER stress and UPR sensors increased in ricolinostat/bendamustine combination treatment.

VII. Bcl-2 Family Proteins and Caspase Pathway are Affected by Ricolinostat/Bendamustine Combination.

Figure 7A:
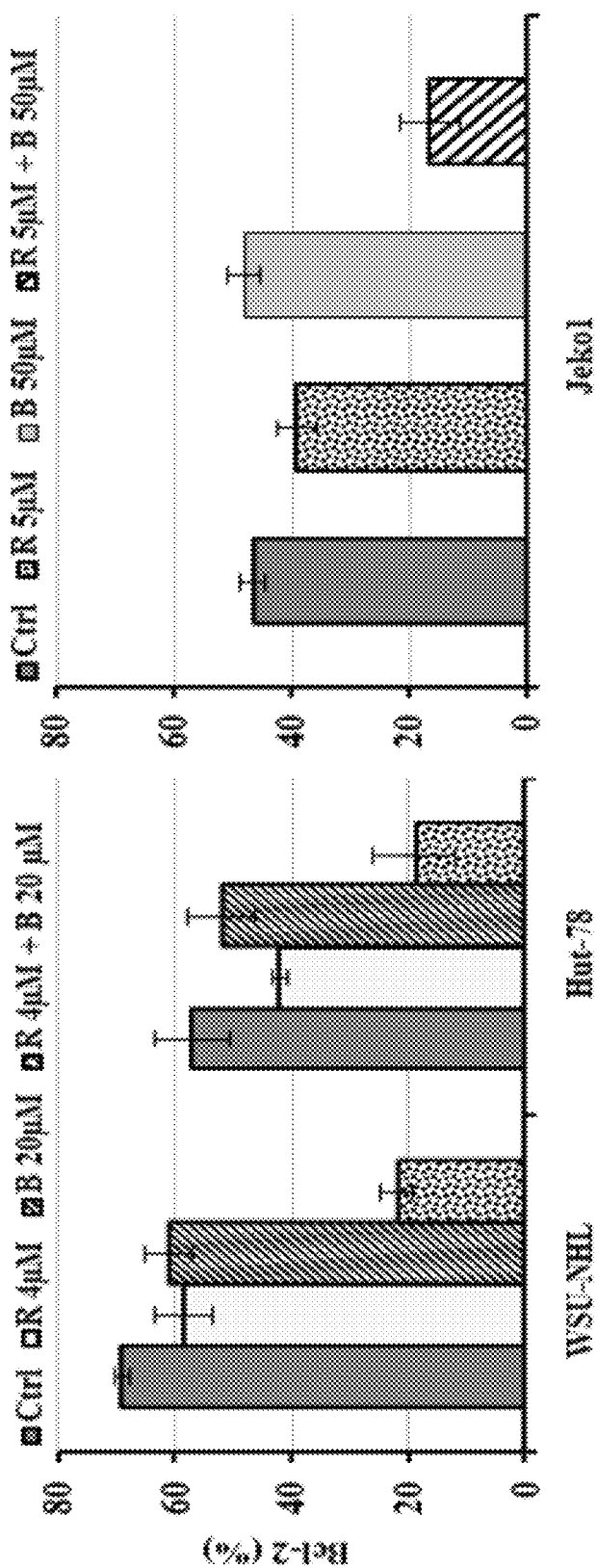
FIG. 7A shows the effect on Bcl-2 protein expression. Ricolinostat (R) and bendamustine (B) decrease expression of Bcl-2. Representative data (%) of Bcl-2 levels in WSU-NHL, Hut-78 and Jeko-1 cells, evaluated by flow cytometry.
Figure 7B:
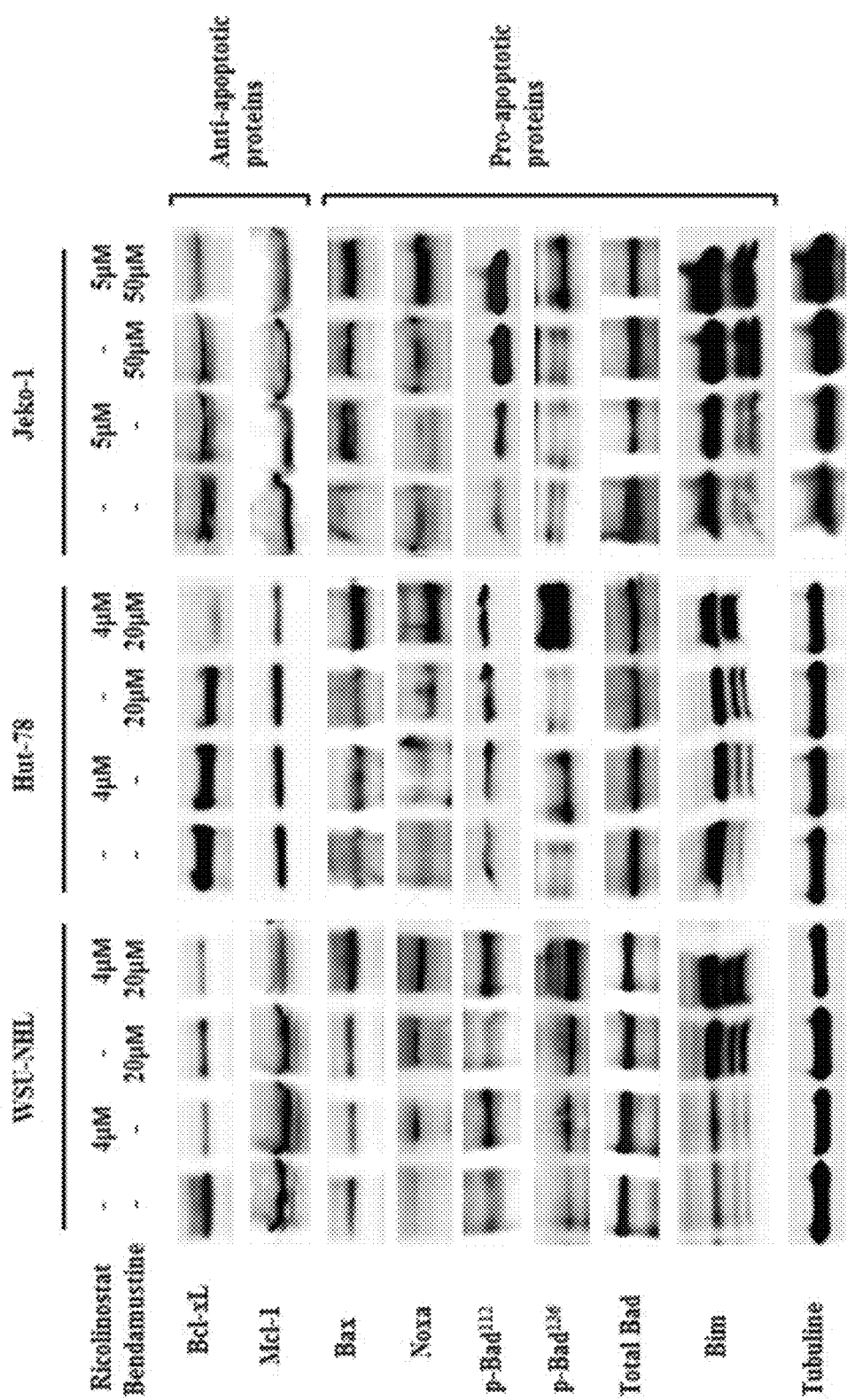
FIG. 7B shows the involvement of Bcl-2 family proteins. Drug combination mediated the down regulation of anti-apoptotic proteins and phosphorylation of the pro-apoptotic proteins. Whole-cell lysates were subjected to western blotting using the indicated Abs.
Figure 7C:
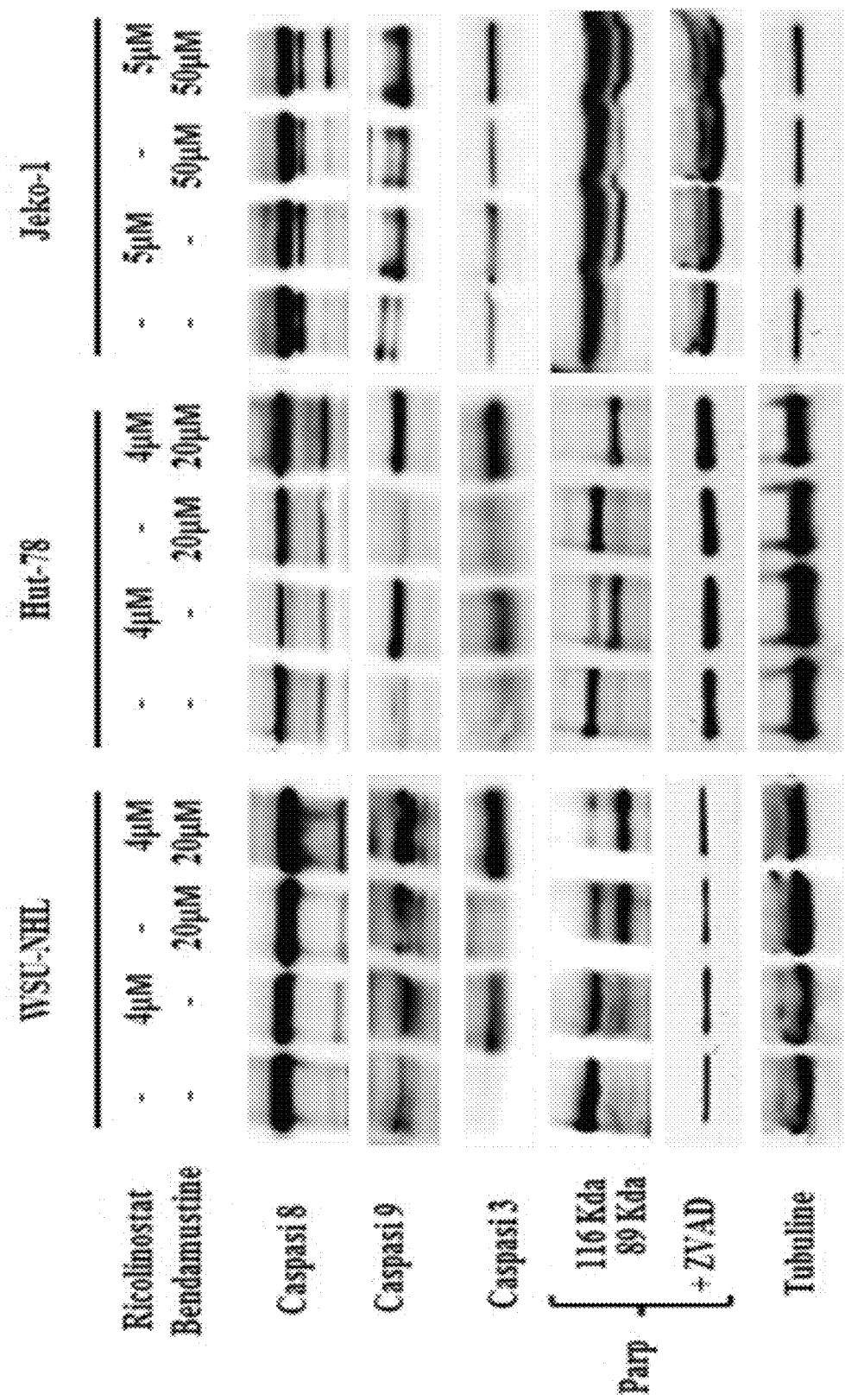
FIG. 7C shows the involvement of the caspase pathway. Representative western blot for caspases-8, -9, -3 and PARP with or without ZVAD-fmk in cellular extracts from WSU-NHL, Hut-78 and Jeko-1 cells. Tubulin is shown as a loading control.

Drug combination reduced Bcl-2 expression (FIG. 7A) and the expression of the antiapoptotic proteins Bcl-xL and Mcl-1 (FIG. 7B). It also increased the levels of the pro-apoptotic members of Bcl-2 family Bax, Bim, Noxa, Bad[112] and Bad[136] (FIG. 7B). The drug combination induced PARP cleavage and activation of caspase-8, -9 and -3 in all three cell lines analyzed (FIG. 7C). The PARP cleavage was completely abrogated by the addition of ZVAD-fmk, confirming that ricolinostat/bendamustine induced apoptosis by activating the caspase pathway (FIG. 7C).

VIII. Co-Exposure to Ricolinostat/Bendamustine Leads to AKT Pathway Inactivation.

Figure 8A:
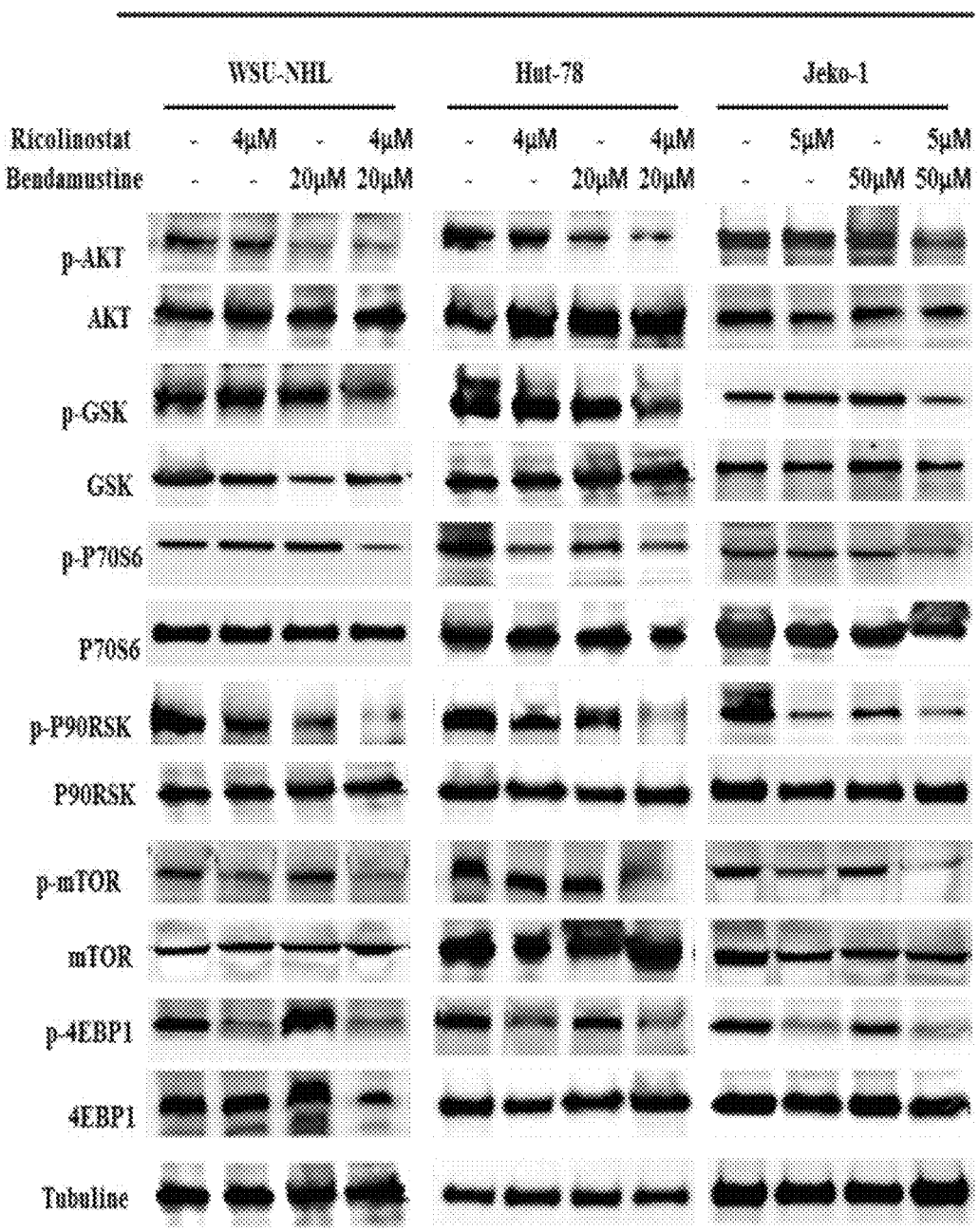
FIG. 8A shows drug combination controls the PI3K/AKT signaling pathways. WSU-NHL and Hut-78 cells treated with 4 µM of ricolinostat and 20 µM bendamustine; Jeko-1 cells treated with 5 µM of ricolinostat and 50 µM of bendamustine. Whole-cell lysates were subjected to western blotting using the indicated Abs.

Combined treatment of lymphoma cells with ricolinostat and bendamustine induced down-regulation of p-AKT and multiple downstream targets (FIG. 8A).

IX. Effect of Ricolinostat Alone and in Combination on HDAC6 Acetylation of α-Tubulin.

Figure 8B:
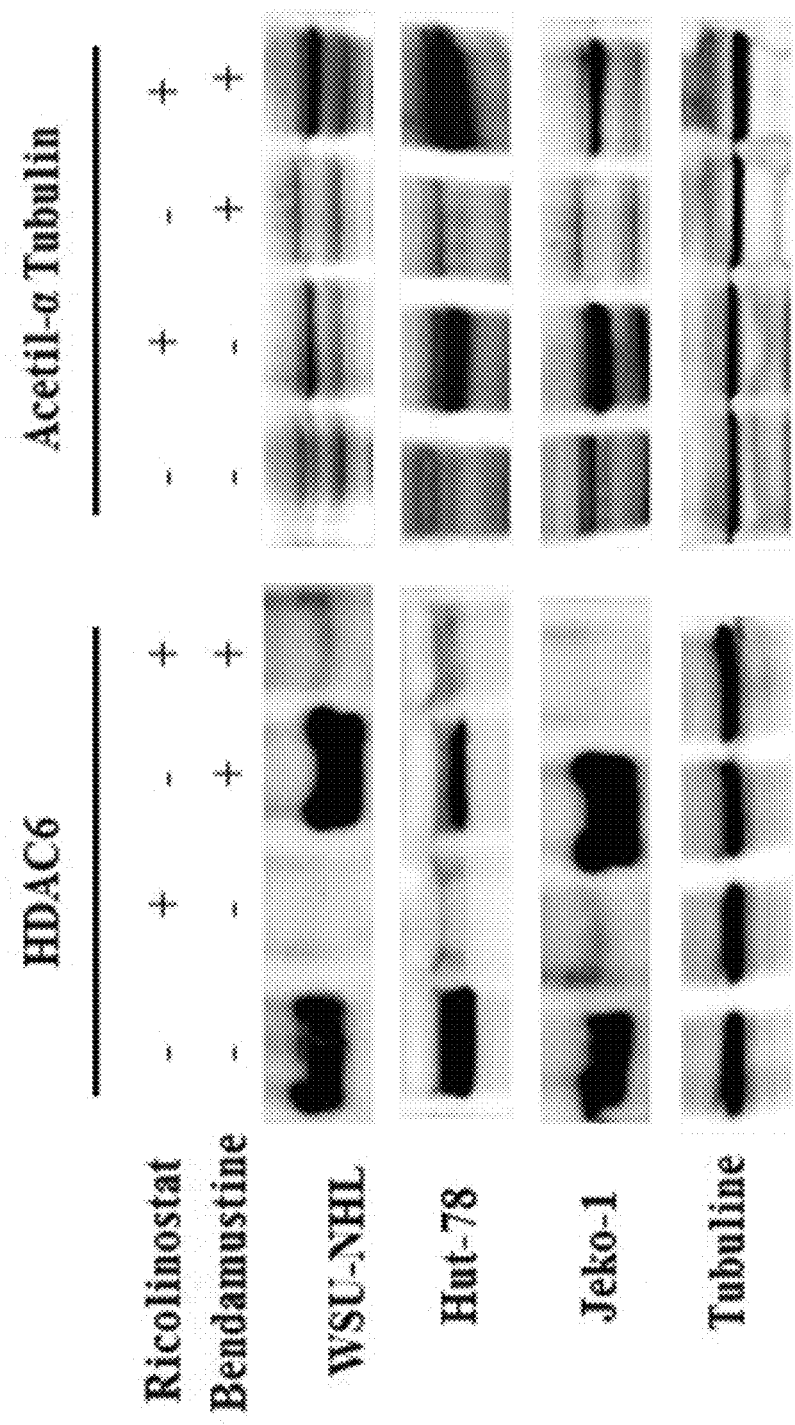
FIG. 8B shows the effect of ricolinostat alone and in combination with bendamustine on HDAC6 acetylation of α-tubulin. The exposure of ricolinostat reduced HDAC6 expression and induced the acetylation level of α-tubulin in lymphoma cells, the extent of which was not further modified by bendamustine. Western blots of cellular extracts from WSU-NHL, Hut-78 and Jeko-1 treated with the drugs alone or in combination for 24 h. Tubulin was used to normalize protein loading.

The exposure to ricolinostat reduced HDAC6 expression and induced the acetylation level of α-tubulin in lymphoma cells, the extent of which was not further modified by bendamustine (FIG. 8B).

X. Ricolinostat Alone and in Combination Stabilizes Microtubules.

Figure 9A:
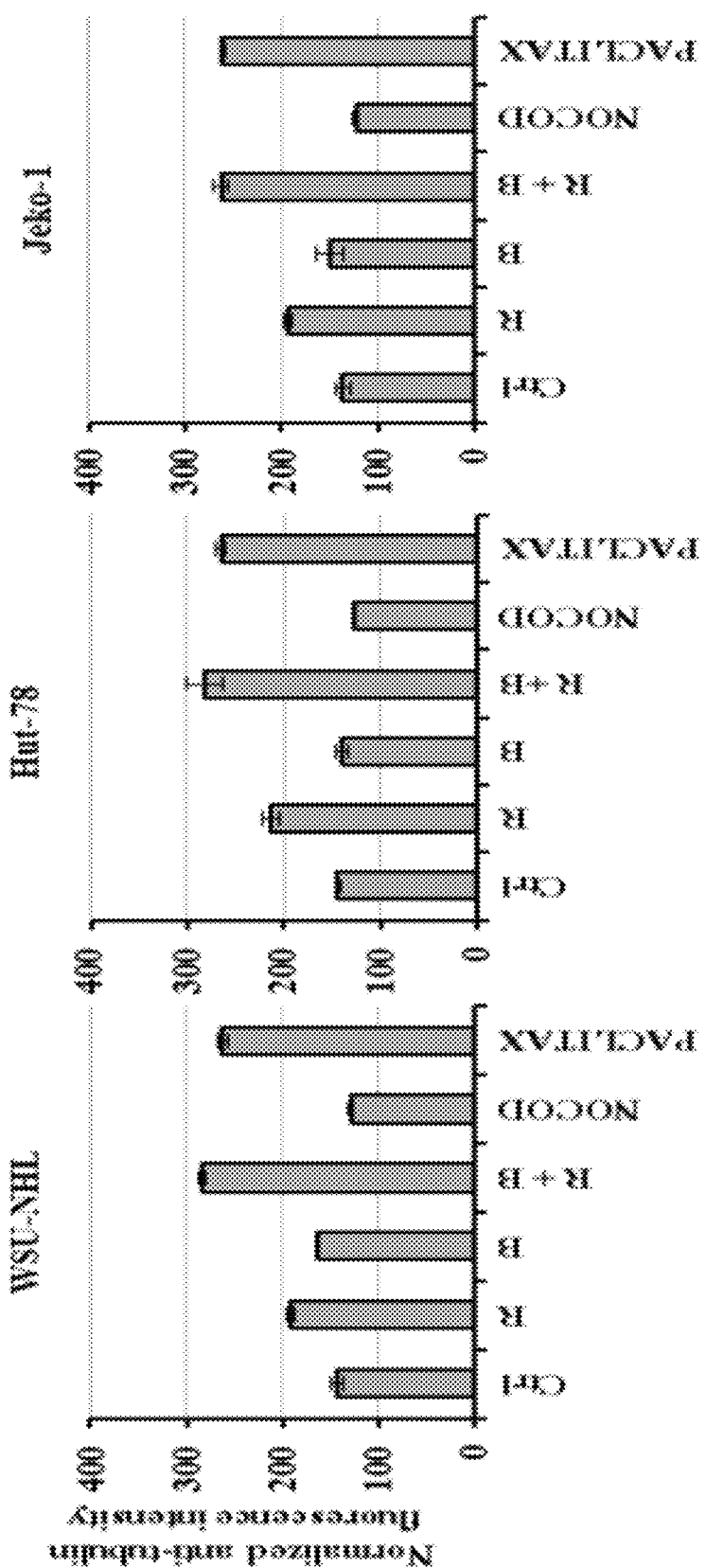
FIG. 9A shows ricolinostat alone and in combination with bendamustine stabilizes microtubules. Ricolinostat alone induced an increase of intensity of fluorescence which is further increased with drug combination. Representative data from analyses of tubulin polymerization assessed by anti-α-tubulin staining and flow cytometry. WSU-NHL and Hut-78 treated for 24 hours with ricolinostat (R) 4 µM and bendamustine (B) 20 µM alone and in combination; Jeko-1 cells treated with ricolinostat 5 µM and bendamustine 50 µM as well as with the microtubule destabilizer nocodazole (negative Ctrl) (1 µM) and the microtubule stabilizer paclitaxel (positive Ctrl) (100 nM). Data are expressed as mean±SD and were obtained from three independent experiments performed in triplicate.

The accumulation of acetylated α-tubulin is associated with increased resistance to microtubule destabilization, which could disrupt the alignment of chromosomes during mitosis and lead to apoptosis. Lymphoma cells were treated for 24 hours with ricolinostat alone and in combination with bendamustine along with the microtubule destabilizer nocodazole (1 μM) and the microtubule stabilizer paclitaxel (100 nM). This was followed by whole cell-based quantitative measurement of tubulin polymerization using alpha-tubulin staining. Ricolinostat alone induced tubulin polymerization as demonstrated by the increase of intensity of fluorescence. The effect was further enhanced by the addition of bendamustine (FIG. 9A).

XI. Ricolinostat Alone and in Combination Down-Modulated IL-10 Expression.

Figure 9B:
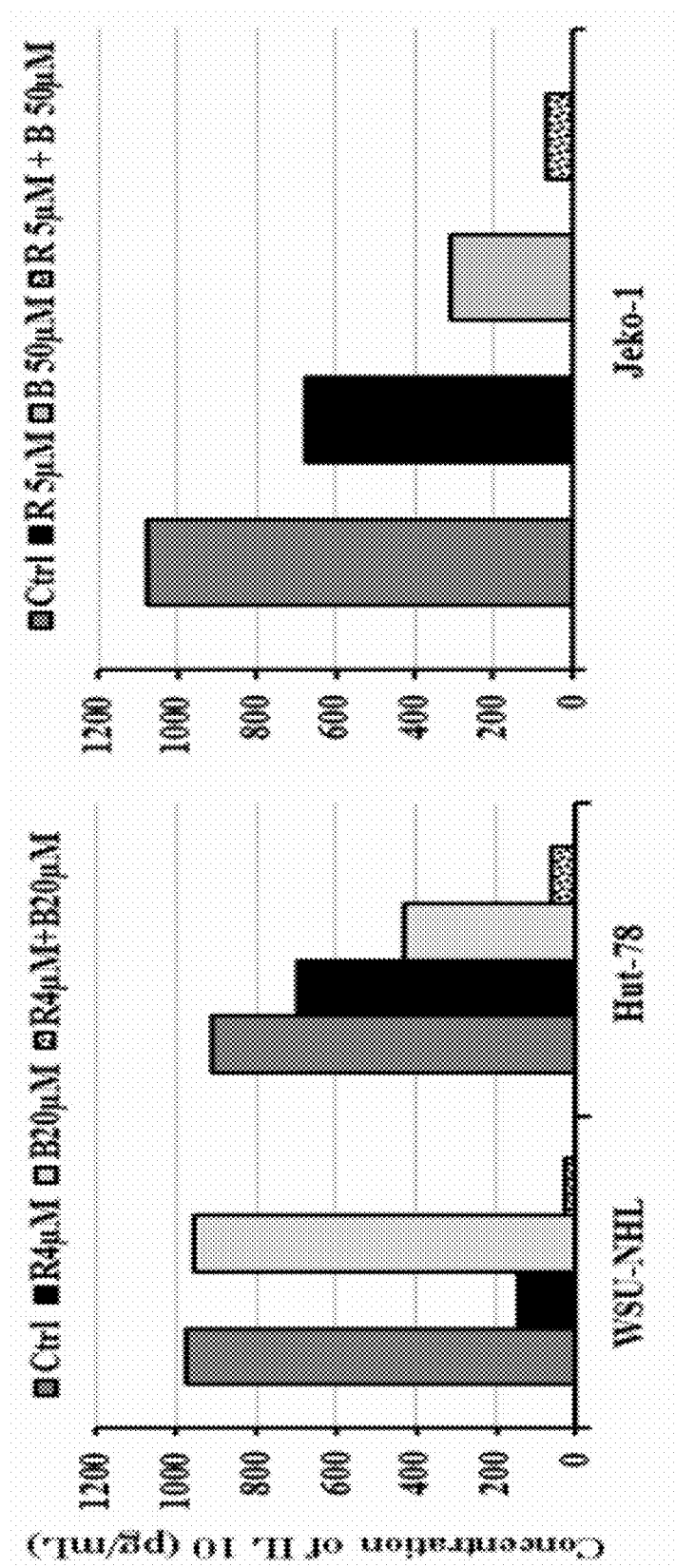
FIG. 9B shows ricolinostat alone and in combination with bendamustine down-modulated IL-10 expression. Effect of drug combination on IL-10 secretion in WSU-NHL, Hut-78 and Jeko-1 cells. Ricolinostat alone induced a down-regulation of IL-10. The drug combination further decreased levels of this cytokine compared with either compound alone. IL-10 secretion was analyzed by ELISA. All data are means (±SD) of at least three separate experiments each performed in duplicate.

IL-10 is a multifunctional cytokine that plays a crucial role in immunity and tolerance. Ricolinostat/bendamustine decreased the levels of this cytokine compared with either compound alone (FIG. 9B) suggesting combination treatment results in a less immunosuppressive microenvironment.

XII. Summary

A summary of the key results follows. Exposure of lymphoma cell lines to Compound A for 24-72 hours resulted in time- and dose-dependent inhibition of cell growth with IC$_{50}$ values ranging from 0.17 to 8.65 μmol/L. A significant cytotoxic effect was evident after 48 hours of ricolinostat incubation by MTT assays with the most sensitive cell lines being WSU-NHL and Hut-78 (IC50: 1.97-1.5 μmol/L) and the least sensitive being Granta-519 (IC50: 20 μmol/L). Ricolinostat alone induced time- and dose-dependent increases in apoptosis. After 48 hours of treatment with doses ranging from 1 to 20 μmol/L, the percentage of apoptotic cells in early and late apoptosis increased from 11% to 56% and induced an increase in the percentage of cells in the G0/G1 phase of the cell cycle compared with untreated controls. Synergy analyses were done using WSU-NHL, HUT-78 and GRANTA-519 cells treated with different concentrations of ricolinostat (0, 2, 4 and 8 μmol/L) in combination with bendamustine (0, 10, 20, 40, 50 and 100 μmol/L) and lymphoma cells were assayed by MTT at 24 and 48 hours. A clear synergistic interaction, confirmed by the Chou-Talalay method, was observed after 24 hours using low concentrations of two drugs, which are lower than their IC$_{50}$ values. Ricolinostat (4 and 8 μmol/L) and bendamustine (20 and 40 μmol/L) showed a synergistic interaction with CI (combination index) values ranging between 0.13 and 0.34 in Hut-78 and WSU-NHL cells. The treatment of GRANTA-519 cells with ricolinostat (20 and 40 μmol/L) with bendamustine (50 and 100 μmol/L) showed CI values of 0.26 and 0.21 respectively. The drug combinations enhanced apoptosis, as assessed by AnnexinV/PI staining. The percentage of apoptosis after 24 hours ranged from 55 to 80%. Furthermore, ricolinostat with bendamustine reduced the proportion of cells in the G0/G1 and S phases and caused an increase of "sub-G0/G1" peak. Finally, the combination of ricolinostat with bendamustine did not trigger relevant decreases in the viability of normal peripheral blood mononuclear cells (PBMNCs).

In conclusion, these preclinical results indicate that ricolinostat can have marked activity in lymphoma cell lines in combination with bendamustine.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A pharmaceutical combination for treating lymphoma comprising a therapeutically effective amount of a histone deacetylase 6 (HDAC6) specific inhibitor or a pharmaceutically acceptable salt thereof, and bendamustine or a pharmaceutically acceptable salt thereof, wherein the HDAC6-specific inhibitor is a compound of Formula I:

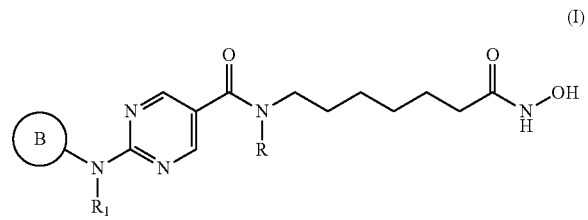

or a pharmaceutically acceptable salt thereof,
wherein
   ring B is aryl or heteroaryl;
   R$_1$ is an aryl or heteroaryl, each of which may be optionally substituted by OH, halo, or C$_{1-6}$-alkyl; and
   R is H or C$_{1-6}$-alkyl.

2. The combination of claim 1, wherein the compound of Formula I is:

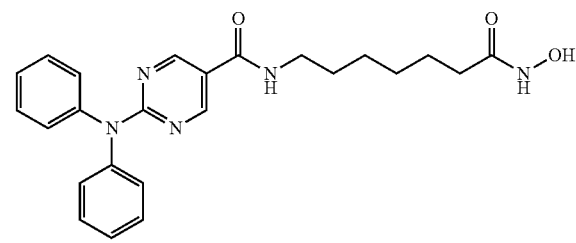 [SMILES: O=C(CCCCCCNC(=O)c1cnc(N(c2ccccc2)c2ccccc2)nc1)NO]

or a pharmaceutically acceptable salt thereof.

3. The combination of claim 1, wherein the compound of Formula I is:

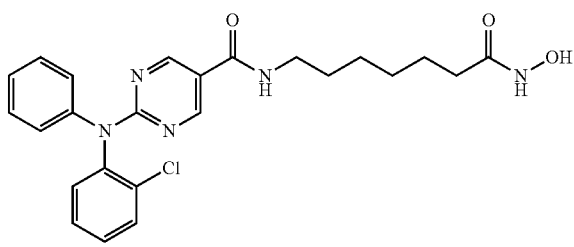 [SMILES: O=C(CCCCCCNC(=O)c1cnc(N(c2ccccc2)c2ccccc2Cl)nc1)NO]

or a pharmaceutically acceptable salt thereof.

4. A method for treating lymphoma in a subject in need thereof, comprising administering to the subject a therapeutically effective amount of a pharmaceutical combination comprising a histone deacetylase 6 (HDAC6) specific inhibitor or a pharmaceutically acceptable salt thereof, and bendamustine or a pharmaceutically acceptable salt thereof, wherein the HDAC6-specific inhibitor is a compound of Formula I:

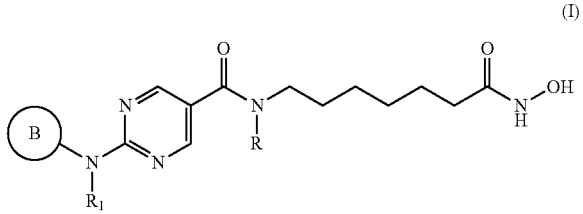

(I)

or a pharmaceutically acceptable salt thereof,
wherein
   ring B is aryl or heteroaryl;
   $R_1$ is an aryl or heteroaryl, each of which may be optionally substituted by OH, halo, or $C_{1-6}$-alkyl; and
   R is H or $C_{1-6}$-alkyl.

5. The method of claim 4, wherein the lymphoma is selected from the group consisting of T-cell lymphoma, cutaneous T-cell lymphoma, anaplastic lymphoma, B-cell lymphoma, follicular lymphoma, and mantle cell lymphoma.

6. The method of claim 4, wherein the compound of Formula I is:

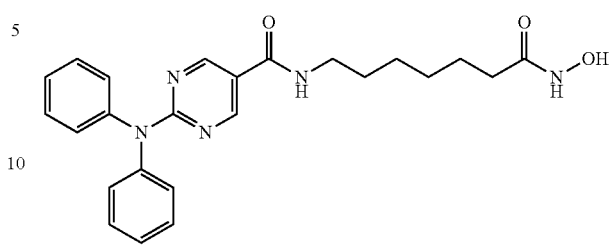

or a pharmaceutically acceptable salt thereof.

7. The method of claim 4, wherein the compound of Formula I is:

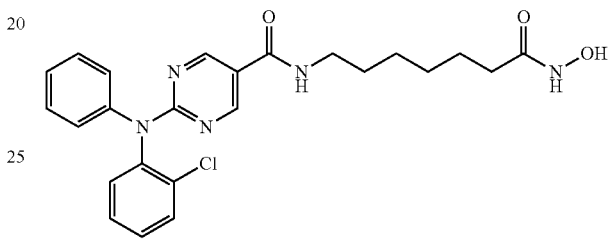

or a pharmaceutically acceptable salt thereof.

8. The method of claim 4, wherein the HDAC inhibitor and bendamustine are administered in separate dosage forms.

9. The method of claim 4, wherein the HDAC inhibitor and bendamustine are administered in a single dosage form.

10. The method of claim 4, wherein the HDAC inhibitor and bendamustine are administered at different times.

11. The method of claim 4, wherein the HDAC inhibitor and bendamustine are administered at substantially the same time.

12. A method for inducing apoptosis of a cancer cell comprising administering to the cell a combination comprising an HDAC inhibitor and bendamustine.

* * * * *